US009023841B2

(12) United States Patent
Akbari

(10) Patent No.: US 9,023,841 B2
(45) Date of Patent: May 5, 2015

(54) COMPOSITIONS AND METHODS FOR THE TREATMENT OF ASTHMA AND ASSOCIATED DISORDERS

(75) Inventor: Omid Akbari, Santa Monica, CA (US)

(73) Assignee: University of Southern California, Los Angeles, CA (US)

(*) Notice: Subject to any disclaimer, the term of this patent is extended or adjusted under 35 U.S.C. 154(b) by 0 days.

(21) Appl. No.: 13/565,644

(22) Filed: Aug. 2, 2012

(65) Prior Publication Data
US 2013/0072475 A1 Mar. 21, 2013

Related U.S. Application Data

(60) Provisional application No. 61/514,850, filed on Aug. 3, 2011.

(51) Int. Cl.
A61K 31/513 (2006.01)
A61K 31/138 (2006.01)
A61K 31/55 (2006.01)
A61K 31/4168 (2006.01)
A61K 38/08 (2006.01)
A61K 38/10 (2006.01)
A61K 38/17 (2006.01)
C07K 14/47 (2006.01)
A61K 31/277 (2006.01)
A61K 31/506 (2006.01)
G01N 33/50 (2006.01)

(52) U.S. Cl.
CPC .............. A61K 31/55 (2013.01); A61K 31/138 (2013.01); A61K 31/4168 (2013.01); A61K 31/513 (2013.01); A61K 38/08 (2013.01); A61K 38/10 (2013.01); A61K 38/1709 (2013.01); C07K 14/4703 (2013.01); A61K 31/277 (2013.01); A61K 31/506 (2013.01); G01N 33/5091 (2013.01); G01N 2800/24 (2013.01)

(58) Field of Classification Search
None
See application file for complete search history.

(56) References Cited

U.S. PATENT DOCUMENTS

2002/0095030 A1 7/2002 Tschopp et al.
2010/0129429 A1 5/2010 Gorski et al.
2011/0104065 A1 5/2011 Espina et al.
2011/0224133 A1 9/2011 Jung et al.
2013/0316958 A1 11/2013 Jung

FOREIGN PATENT DOCUMENTS

WO WO 2006/010041 A2 1/2006
WO WO 2010/011952 1/2010
WO WO 2010/011952 A2 * 1/2010
WO WO 2010/022236 A2 2/2010
WO WO 2012/015836 2/2012

OTHER PUBLICATIONS

Lomia et al. (Bronchial asthma as neurogenic paroxysmal inflammatory disease: A randomized trial with carbomezepine., Respiratory Medicine (2006) vol. 100 pp. 1988-1996).*
Inoue et al. (Inducible disruption of autophagy in the lung causes airway hyper-responsiveness., Biochem and Biophys Research Communications, vol. 405 (Feb. 15, 2011), pp. 13-18).*
Takamura et al. (Autophagy-deficient mice develop multiple liver tumors., Genes and Development (Apr. 15, 2011), vol. 25, pp. 795-800).*
American Lung Association (ALA) (http://www.lung.org/lung-disease/list.html Accessed Mar. 2, 2014.*
van der Worp et al. PLOS Medicine, Mar. 2010, vol. 7 (3)).*
Database WPI Week 200751, 2007-514150.
Deretic et al., "How Cells Clean House." Sci. Am. 298:74-81 (2008).
Glykofrydes et al., "Herpes virus Saimiri vFLIP Provides an Antiapoptotic Function but Is Not Essential for Viral Replication, Transformation, or Pathogenicity," Journal of Virology 74(24):11919-11927 (2000).
Gozuacik et al., "Autophagy as a cell death and tumor suppressor mechanism" Oncogene 23:2891-2906 (2004).
Guasparri et al. "The KSHV oncoprotein vFLIP contains a TRAF interacting motif and requires TRAF2 and TRAF3 for signaling." EMBO Rep. 7:114-119 (2006).
Lee et al., "FLIP-mediated autophagy regulation in cell death control," Nature Cell Biology 11(11):1355-1362 (2009).
Levine et al., "Autophagy in the Pathogenesis of Disease" Cell 132:27-42 (2008).
Levine et al., "Development by Self-Digestion: Molecular Mechanisms and Biological Functions of Autophagy" Dev. Cell 6:463-477 (2004).
Liang et al., "Autophagic and tumour suppressor activity of a novel Beclin1-binding protein UVRAG" Nat. Cell Biol. 8:688-699 (2006).
Matta et al., "Activation of alternative NF-kB pathway by human herpes virus 8-encoded Fas-associated death domainlike IL-1.-converting enzyme inhibitory protein (vFLIP)" Proc. Natl. Acad. Sci. USA 101:9399-9404 (2004).
Mizushima et al., "Autophagy fights disease through cellular self-digestion" Nature 451:1069-1075 (2008).
Rubinsztein et al., "Potential therapeutic applications of autophagy" Nat. Rev. Drug Discov. 6:304-312 (2007).
Shintani et al., "Autophagy in health and disease: a double-edged sword," Science 306:990-995 (2004).
Sir et al., "Autophagy in viral replication and pathogenesis," Molecules and Cells, 1-7 (2010).
Taylor et al., "Inhibition of the Death Receptor Pathway by cFLIP Confers Partial Engraftment of MHC Class I-Deficient Stem Cells and Reduces Tumor Clearance in Perforin-Deficient Mice." Journal of Immunology 167:4230-4237 (2001).

(Continued)

Primary Examiner — James H Alstrum Acevedo
Assistant Examiner — Tara Martinez
(74) Attorney, Agent, or Firm — Foley & Lardner LLP; Antoinette F. Konski

(57) ABSTRACT

This disclosure provides methods for treating asthma or an associated disorder in a patient in need thereof, by administering to the patient an effective amount of an autophagy inducing agent, thereby treating the asthma or the associated disorder. Disorders that can be treated include, allergic asthma, chronic obstructive pulmonary disease, lung inflammation, respiratory tolerance and a lung infection or disorder.

7 Claims, 15 Drawing Sheets

(56) References Cited

OTHER PUBLICATIONS

Thorne et al., "Regulation of Lymphocyte Proliferation and Death by Flip" Nat. Rev. Immunol. 1:50-58 (2001).

Ye et al., "Kaposi's sarcoma-associated herpes virus latent gene vFLIP inhibits viral lytic replication through NF-kappa B-mediated suppression of the AP-1 pathway: a novel mechanism of virus control of latency," Journal of Virology 82(9): 4235-4249 (2008).

Yu et al., "Regulation of an ATG7013beclin 1 Program of Autophagic Cell Death by Caspase-8" Science 304:1500-1502 (2004).

Akbari, O. et al. (2010) "PD-L1 and PD-L2 modulate airway inflammation and iNKT-cell-dependent airway hyperreactivity in opposing directions," Mucosal Immunol 3(1):81-91.

Bushell, M. et al. (2008) "SF2/ASF TORCS Up Translation," Molecular Cell 30:262-263.

Cadwell, K. et al. (2008) "A key role for autophagy and the autophagy gene Atg16l1 in mouse and human intestinal Paneth cells," Nature 456:259-263.

Cadwell, K. et al. (2009) "A common role for Atg16L1, Atg5 and Atg7 in small intestinal Paneth cells and Crohn disease," Autophagy 5(2):250-252.

Chen, Z.H. et al. (2008) "Egr-1 regulates autophagy in cigarette smoke-induced chronic obstructive pulmonary disease," PLoS One 3:e3316.

Chen, Z.H. et al. (2010) "Autophagy protein microtubule-associated protein 1 light chain-3B (LC3B) activates extrinsic apoptosis during cigarette smoke-induced emphysema," Proc Natl Acad Sci USA 107:18880-18885.

Fleming, A. et al. (2011) "Chemical modulators of autophagy as biological probes and potential therapeutics," Nat Chem Biol 7:9-17.

Fujita, N. et al. (2008) "The Atg16L complex specifies the site of LC3 lipidation for membrane biogenesis in autophagy," Mol Biol Cell 19:2092-2100.

Gutierrez, M.G. et al. (2004) "Autophagy is a defense mechanism inhibiting BCG and *Mycobacterium tuberculosis* survival in infected macrophages," Cell 119:753-766.

Hadeiba, H. et al. (2003) "Lung CD25 CD4 regulatory T cells suppress type 2 immune responses but not bronchial hyperreactivity," J Immunol 170:5502-5510.

Hidvegi, T. et al., (2010) "An autophagy-enhancing drug promotes degradation of mutant alpha1-antitrypsin Z and reduces hepatic fibrosis," Science 329:229-232.

Hwang, J.W. et al. (2010) "Cigarette smoke-induced autophagy is regulated by SIRT1-PARP-1-dependent mechanism: implication in pathogenesis of COPD," Arch Biochem Biophys 500:203-209.

International Search Report (ISA/KR) for International Application No. PCT/US2012/049381, mailed Dec. 20, 2012.

Jung, H.S. et al. (2008) "Loss of autophagy diminishes pancreatic beta cell mass and function with resultant hyperglycemia," Cell Metab 8:318-324.

Kim, H.P. et al. (2008) "Autophagic proteins regulate cigarette smoke-induced apoptosis: protective role of heme oxygenase-1," Autophagy 4(7):887-895.

Korfhagen, T.R. et al. (1990) "Cis-acting sequences from a human surfactant protein gene confer pulmonary-specific gene expression in transgenic mice," Proc Natl Acad Sci USA 87:6122-6126.

Kuma, A. et al. (2004) "The role of autophagy during the early neonatal starvation period," Nature 432:1032-1036.

Okubo, T. et al. (2005) "Nmyc plays an essential role during lung development as a dosage-sensitive regulator of progenitor cell proliferation and differentiation," Development 132:1363-1374.

Pyo, J.O. et al. (2005) "Essential Roles of Atg5 and FADD in Autophagic Cell Death," J Biol Chem 280(21):20722-20729.

Rossi, M. et al. (2009) "Desmethylclomipramine induces the accumulation of autophagy markers by blocking autophagic flux," J Cell Sci 122:3330-3339.

Williams, A. et al. (2008) "Novel targets for Huntington's disease in an mTOR-independent autophagy pathway," Nat Chem Biol 4:295-305.

Yang, Z. et al. (2009) "An overview of the molecular mechanism of autophagy," Curr Top Microbiol Immunol 335:1-32.

Zhang, L. et al. (2007) "Small molecule regulators of autophagy identified by an image-based high-throughput screen," Proc Natl Acad Sci USA 104:19023-19028.

\* cited by examiner

** $P<0.005$

* P<0.01

COMPOSITIONS AND METHODS FOR THE TREATMENT OF ASTHMA AND ASSOCIATED DISORDERS

CROSS-REFERENCE TO RELATED APPLICATIONS

This application claims the benefit under 35 U.S.C. §119 (e) of U.S. Provisional Application Ser. No. 61/514,850, filed Aug. 3, 2011, the contents of which is hereby incorporated by reference in its entirety.

SEQUENCE LISTING

The instant application contains a Sequence Listing which has been submitted in ASCII format via EFS-Web and is hereby incorporated by reference in its entirety. Said ASCII copy, created on Oct. 25, 2012, is named 06418949.txt and is 18,377 bytes in size.

STATEMENT OF FEDERAL SUPPORT

This invention was made with government support under the Grant No. 5RO1A1066020, awarded by the National Institutes of Health. Accordingly, the U.S. Government has certain rights to the invention.

BACKGROUND

Throughout this disclosure, various patent and technical publications are identified by an identifying citation. These citations and the publications referenced within the present specification are incorporated by reference into the present disclosure to more fully describe the state of the art to which this invention pertains.

Asthma affects 17 million individuals in the United States including 5 million children or according to US Centre for Disease Control 8.2% of the US population in 2009 and is responsible for $50 billion in medical costs. The prevalence of asthma in children has dramatically increased over the last 20 years, which will result in a heightened burden in the future. Asthma represents a profound burden on healthcare provisions estimated to be responsible for 9 million visits to healthcare providers, nearly 2 million emergency room visits and almost half a million hospitalizations. Although many aspects in the development of asthma have now been elucidated, the underlying cause is still unclear. This means that current therapeutic options for treatment rely on symptom management by reducing airway inflammation and the use of bronchiole dilators. However, these treatments may actually lead to disease exacerbation in the long run.

Allergic symptoms are clinical manifestations of an atopic, allergen-specific immune response. A central tenet in this paradigm is the deviation of allergen-responsive naïve T helper cells away from a tolerant or hypo-responsive mode towards a TH2-polarized effector pathway (characterized by secretion of TH2 cytokines, such as IL-4, IL-5, and IL-13). However, the mechanisms that underlie polarization towards a TH2 response are not fully understood but are thought to be partially dependant on the avidity of the antigen, cytokines released by antigen presenting cells and co-stimulatory/inhibitory molecule interactions. Macroautophagy (hereafter referred to as autophagy) is the intracellular process by which damaged organelles are cleared and recycled and is crucial for cellular survival to starvation (Deretic et al. (2009) Cell Host Microbe 5:527-549; Yang et al. (2009) Curr Top Microbiol Immunol 335:1-32; Yang et al. (2010) Nat Cell Biol 12:814-822). Increasing evidence now suggests that pathogens can inhibit autophagy to prevent their destruction or paradoxically may hijack autophagy to increase infectivity (Kim et al. (2010) Semin Immunopathol 32:323-341). In addition the breakdown of pathogens by autophagy is required for the generation of peptides that can be presented to the immune system to stimulate the adaptive immune system (Lee et al. (2010) Immunity 32:227-239; Paludan et al. (2005) Science 307:593-596) and release of other pathogen components, which can activate pattern recognition receptors of the innate immune system (Jounai et al. (2007) Proc Natl Acad Sci USA 104:14050-14055; Lee et al. (2007) Science 315:1398-1401). Defects in autophagy results in an inability to recycle damaged organelles with the potential release of reactive oxygen species (Tal et al. (2009) Proc Natl Acad Sci USA 106:2770-2775) and other cellular components and is also associated with impaired apoptosis and clearance of dying cells (Qu et al. (2007) Cell 128:931-946). Both of these can lead to activation of the immune system and the development of autoimmune disorders. Therefore, autophagy is a crucial cellular process for survival and in addition in the establishment of innate and adaptive immune responses (Levine et al. (2011) Nature 469:323-335).

Emerging evidence suggests that autophagy is involved in numerous aspects of human health such as infection, aging, cancer, neurodegenerative diseases and is a fundamental homeostatic mechanism that can be adaptive or maladaptive so as to promote health or disease (Yang et al. (2009) Curr Top Microbiol Immunol 335:1-32). Several recent reports suggest that autophagy is involved in cigarette smoke induced apoptosis that underlies part of the pathogenic cascade of chronic obstructive pulmonary disease (Chen et al. (2008) PLoS One 3:e3316; Chen et al. (2010) Proc Natl Acad Sci USA 107: 18880-18885; Hwang et al. (2010) Arch Biochem Biophys 500:203-209; Kim et al. (2008) Autophagy 4:887-895). However, there are as yet no reports regarding the role of autophagy in the development of asthma. Interestingly, carbamazepine a FDA-approved anticonvulsant, which can induce autophagy, has been shown to improve asthma by an unknown mechanism (Lomia et al. (2006) Respir Med 100: 1988-1996). Therefore a determination of the role of autophagy in the airways will provide new concepts relevant to asthma disease pathogenesis and treatment.

SUMMARY

Current therapeutic options for TH2-mediated diseases are limited. The standard clinical care for allergic asthma includes bronchodilators and immunosuppressive drugs that usually must be administered indefinitely as their effects are not long lasting, are ineffective in some patients and may actually exacerbate disease severity (Fu et al. (2009) Eur J Cell Biol 88:215-226; Luciani et al. (2010) Nat Cell Biol 12:863-875). Many treatment options exist to manage other allergy symptoms, but induction of autophagy in patients with asthma has the potential to result in a long lasting cure. Applicant now shows that manipulation of autophagy pathways offers a new therapeutic strategy for patients with allergic asthma and these studies provide novel therapies.

To that end, this disclosure provides compositions and methods to correct regulation of autophagy in numerous human conditions including certain disorders affecting the lungs. For example, it has been shown that autophagy is involved in cigarette smoke induced apoptosis that is part of the pathogenic process associated with chronic obstructive pulmonary disease (Chen et al. (2008) PLoS One 3:e3316; Chen et al. (2010) Proc Natl Acad Sci USA 107:18880-

18885; Hwang et al. (2010) Arch Biochem Biophys 500:203-209; Kim et al. (2008) Autophagy 4:887-895). In addition autophagy has been demonstrated to function in the clearance of defective CFTR protein (Cadwell et al. (2008) Nature 456:259-263; Cadwell et al. (2009) Autophagy 5:250-252), and through extrapolation from the intestine and pancreas, autophagy may play a vital role in the function of the secretary epithelial cells such as goblet cells in the lungs (Jung et al. (2008) Cell Metab 8:318-324; Hidvegi et al. (2010) Science 329:229-232; Rossi et al. (2009) J Cell Sci 122:3330-3339).

In one aspect, provided is a method for treating asthma or an associated disorder in a patient in need thereof, comprising, or alternatively consisting essentially of, or yet further consisting of, administering to the patient an effective amount of an autophagy inducing agent, thereby treating the asthma or the associated disorder. In one aspect, the asthma is allergic asthma. In a further aspect, the related disorder is one or more of chronic obstructive pulmonary disease, lung inflammation, respiratory tolerance and a lung infection or disorder.

This disclosure also provides a transgenic mouse defective in Atg5 protein function.

Yet further provided is a method for screening a compound or agent for the ability to treat asthma or a related disorder comprising, or alternatively consisting essentially of, or yet further consisting of, administering to a suitable animal model a candidate agent for an effective amount of time, and assaying for improved lung function, wherein if the animal has improved lung function, the compound or agent is a candidate for the treatment of asthma or a related disorder. In one aspect, the animal is a mouse, e.g., a transgenic mouse defective in Atg5 protein function.

Also provided is a kit for treating asthma or an associated disorder in a patient in need thereof, comprising, or alternatively consisting essentially of, or yet further consisting of, an autophagy inducing agent and optionally, instructions for use. In another aspect, a composition is provided that comprises, or alternatively consists essentially of, or yet further consists of, an effective amount of an autophagy inducing agent for the treatment of asthma or an associated disorder and a pharmaceutically acceptable carrier. In one aspect, the composition is formulated for local administration, e.g., by inhalation.

BRIEF DESCRIPTION OF THE FIGURES

FIG. 1A shows the scheme for deletion of Atg5 and induction of AHR is indicated. FIG. 1B shows AHR was determined by invasive plethysmography and is expressed as lung resistance (RL, right) and dynamic compliance (Cdyn, left) for C57B16/J (WT) or Atg5flox/flox rosa26Cre ERT after deletion by tamoxifen i.p. (Atg5Δ). FIG. 1C shows representative lung histopathology images are shown after sections have been stained with H&E. Intraperitoneal (i.p.), intranasal (i.n.), representative data from two experiments, mean±SEM with 4 mice per group.

In FIG. 2A, a protocol is described for Atg5flox/flox rosa26Cre ERT with the deletion of Atg5 with i.p. tamoxifen followed by i.n. HDM lysate. FIG. 2B is an outline of the method for Atg5flox/flox sftpC cre. FIG. 2C illustrates the protocol to induce asthma in BALB/c mice by HDM.

FIG. 3A is a schematic for the sensitization and challenge protocol with administration of autophagy inhibitors and inducers via i.p. injection. FIGS. 3B and C show AHR was determined by whole body plethysmography and is expressed as mean PenH in the presence or absence of (FIG. 3B) autophagy inhibitor desmethylclomipramine ("DCMI") 1 mg/kg or (FIG. 3C) autophagy inducers tamoxifen 100 μM, clonidine 0.1 mg/kg or carbamazepine 20 mg/kg. FIGS. 3D and E are a quantitative determination of cellular infiltration into BAL was determined by cytospin preparation in the presence or absence of (FIG. 3D) autophagy inhibitor and (FIG. 3E) autophagy inducers. Representative data from two independent experiments with 3 mice per group, expressed as mean±SEM. PBS refer to naïve BALB/c animals. Figure legend: Total: Total of number of cells in the BAL, PMN: polymorphonuclear cells, EOS: Eosinophils, MACRO: Macrophages, Lymph: Lymphocytes

FIG. 5A is a general scheme for induction of tolerance and induction of AHR. FIG. 5B shows proliferation of T cells after in vitro restimulation with OVA was determined by 3H thymidine incorporation and expressed as mean±SEM with 4 mice per group.

FIG. 7A is a brief description of the protocol used to generate this data. In 7B, a group of BALB/c mice (n=5) were immunized intraperitoneally (i.p.) on day 1 with 50 μg of OVA in 2 mg of Alum and subsequently challenged intranasally (i.n.) with 50 μg of OVA on days 11, 12 and 13. On days 10, 11, 12 and 13, mice were treated i.p. with either rapamycin (100 ng), vFLIP α4-peptide (300 μg) or peptide control TAT (300 μg). The mice were assessed for AHR development, 24 h after the last intranasal challenge (day 14), by measuring the PenH in conscious mice. The X axis shows airway hyperreactivity (AHR), a cardinal feature of asthma, that is always diagnosed and measured in clinic and on animal models, using increasing doses of methacholine. Methacholine is an agent that, when inhaled, causes the airways to spasm and narrow if asthma is present. During this test, subjects inhale increasing amounts of methacholine aerosol mist (or nebulized methacholine) with few minutes intervals, and lung function is measured such as enhanced pause (PehH). Data are mean+/−sem, (n=5) with **P<0.01.

Thereafter, lung sections were stained with hematoxylin and eosin (HE) from the different groups in the HDM and OVA models. Airway inflammation and remodeling were decreased in the HDM/OVA+vFLIP compared to OVA/HDM alone based on smooth muscle hyperplasia, epithelial cell proliferation, subepithelial fibrosis and basement membrane thickening. Thus, the vFLIP peptide effectively reduced cardinal features of asthma in both HDM and OVA models.

Figure 10A:
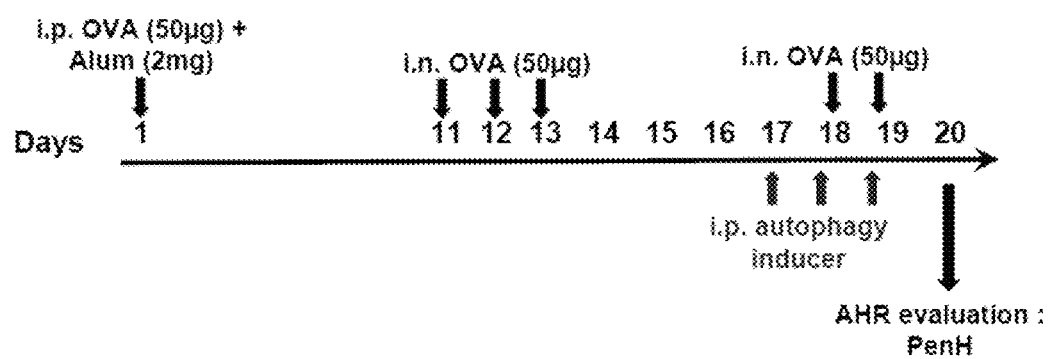
Figure 10B:
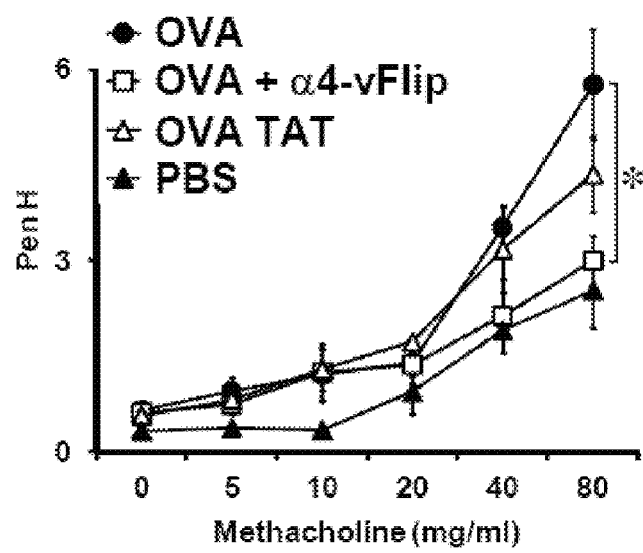

FIG. 10A shows that chronic AHR is impaired by autophagy inducer. BALB/c mice were treated with OVA to induce chronic AHR and administered a4-TAT-vFLIP (as autophagy inducer) and TAT (as irrelevant peptide, control). AHR was assessed by Pen H (enhanced pause). FIG. 10B shows decreased levels of AHR were shown with a4-TAT-vFLIP treated mice, suggesting modulation of autophagy decrease chronic AHR.

Figure 11A:
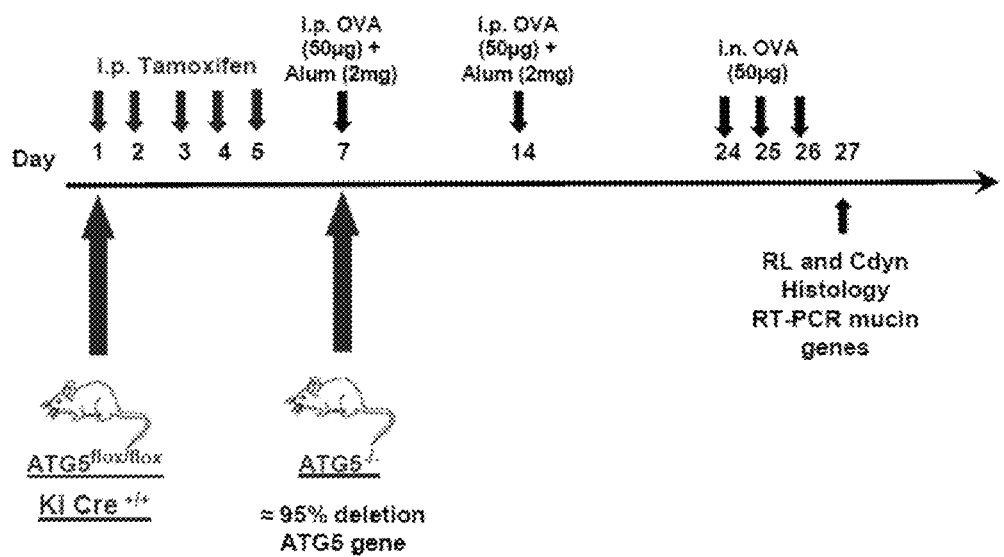
Figures 11B, 11C:
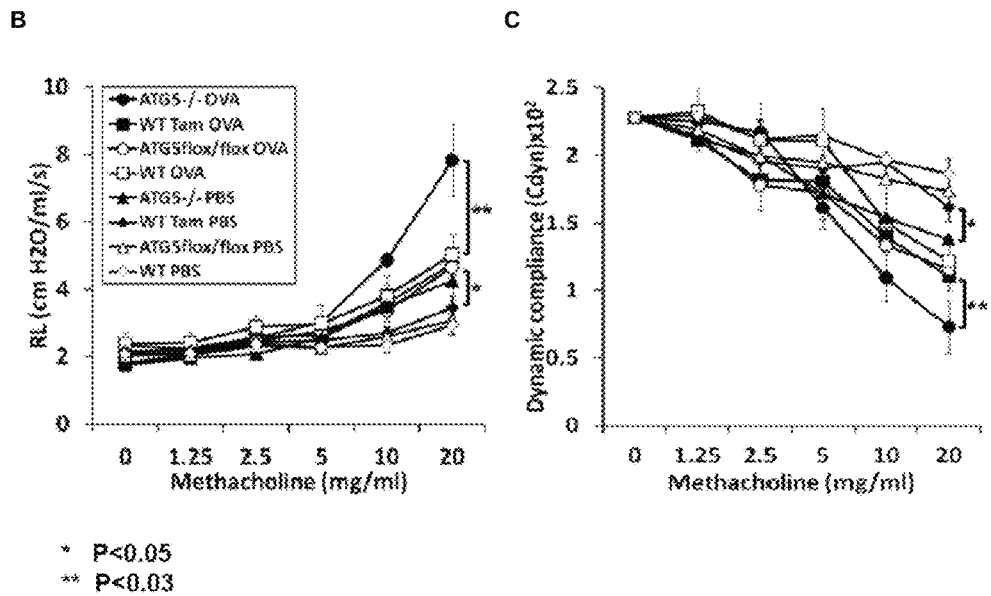

FIG. 11A illustrates a protocol to induce asthma with conditional ATG5−/− mice. Atg5 gene was depleted by administration of Tamoxifen to Atg5flox/flox Ki Cre+/+ mice, then OVA were injected to induce AHR. AHR was subsequently assessed by plethysmography to measure lung resistance (RL), dynamic compliance (Cdyn). Lungs were stained with hematoxylin and eosin (HE). FIGS. 11B and 11C shows that depletion of Atg5 Increased AHR. Conditional Atg5−/− mice, administered Tamoxifen to Atg5flox/flox mice, treated with OVA demonstrated increased levels of RL and decreased levels of Cdyn, suggesting blockade of autophagy exacerbate AHR.

Figure 12:
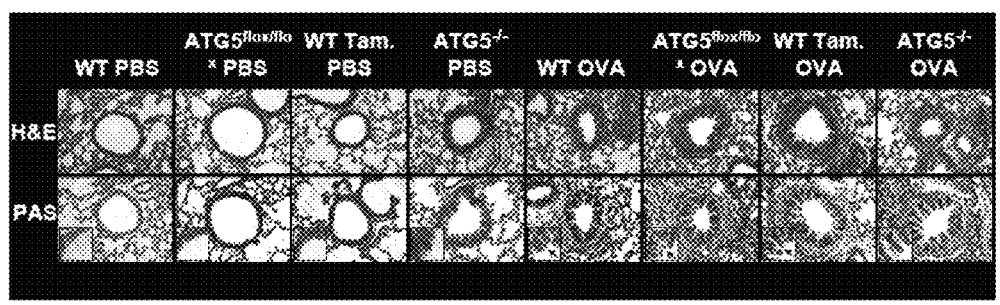

FIG. 12 is a panel showing histology of the lungs in ATG5−/− mice. The results show that blockade of Atg5 exacerbates lung inflammation. BALB/c mice and Atg5flox/flox mice were administrated with or without Tamoxifen, then treated with PBS or OVA in the absence of OVA. Lung tissues were stained with hematoxylin and eosin (HE). Conditional Atg5−/− mice, administered Tamoxifen to Atg5flox/flox mice, treated with OVA showed significant bronchial wall thickness. These findings suggesting blockade of autophagy exacerbate lung inflammation in asthma.

Figure 13A:
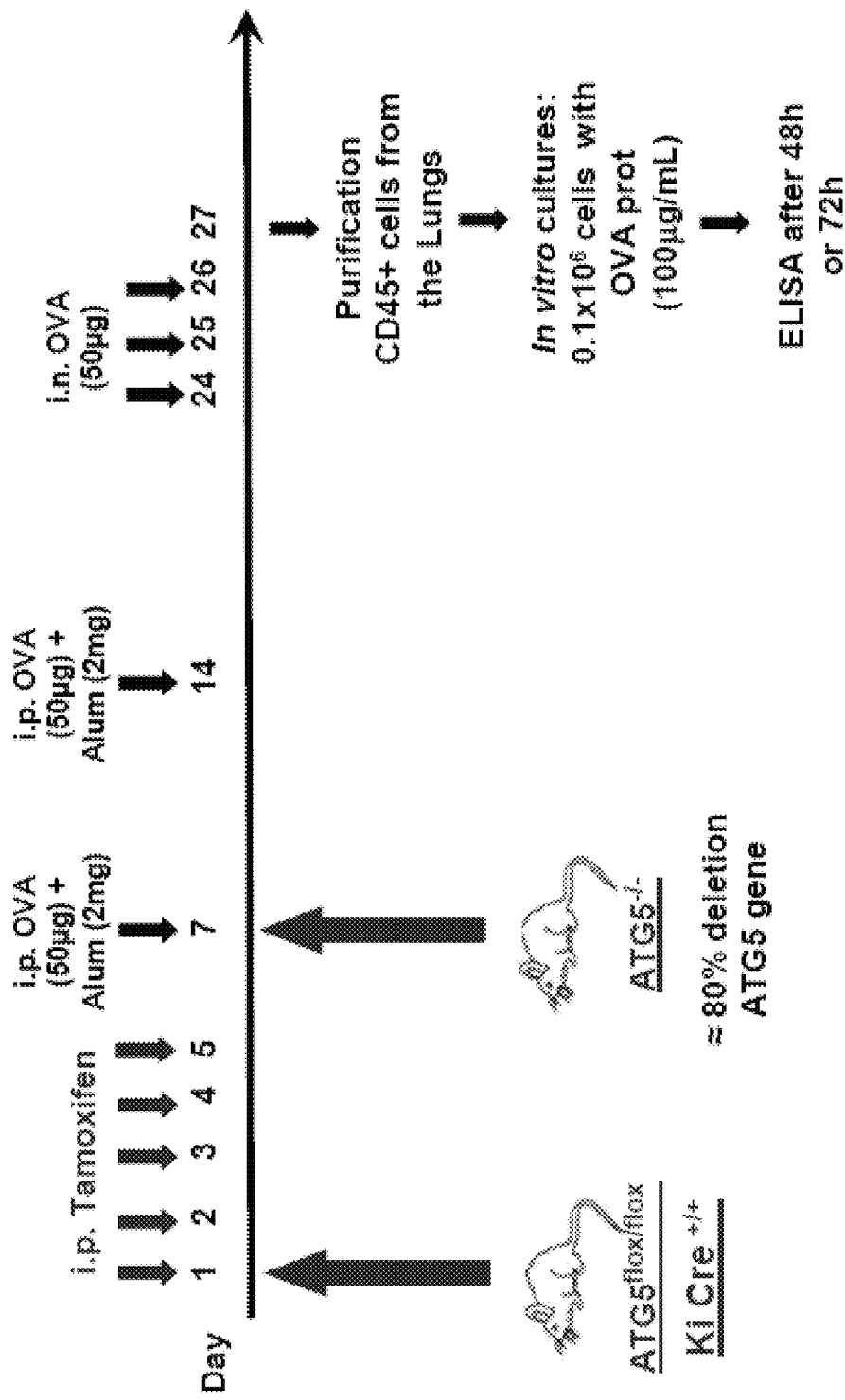
Figure 13B:
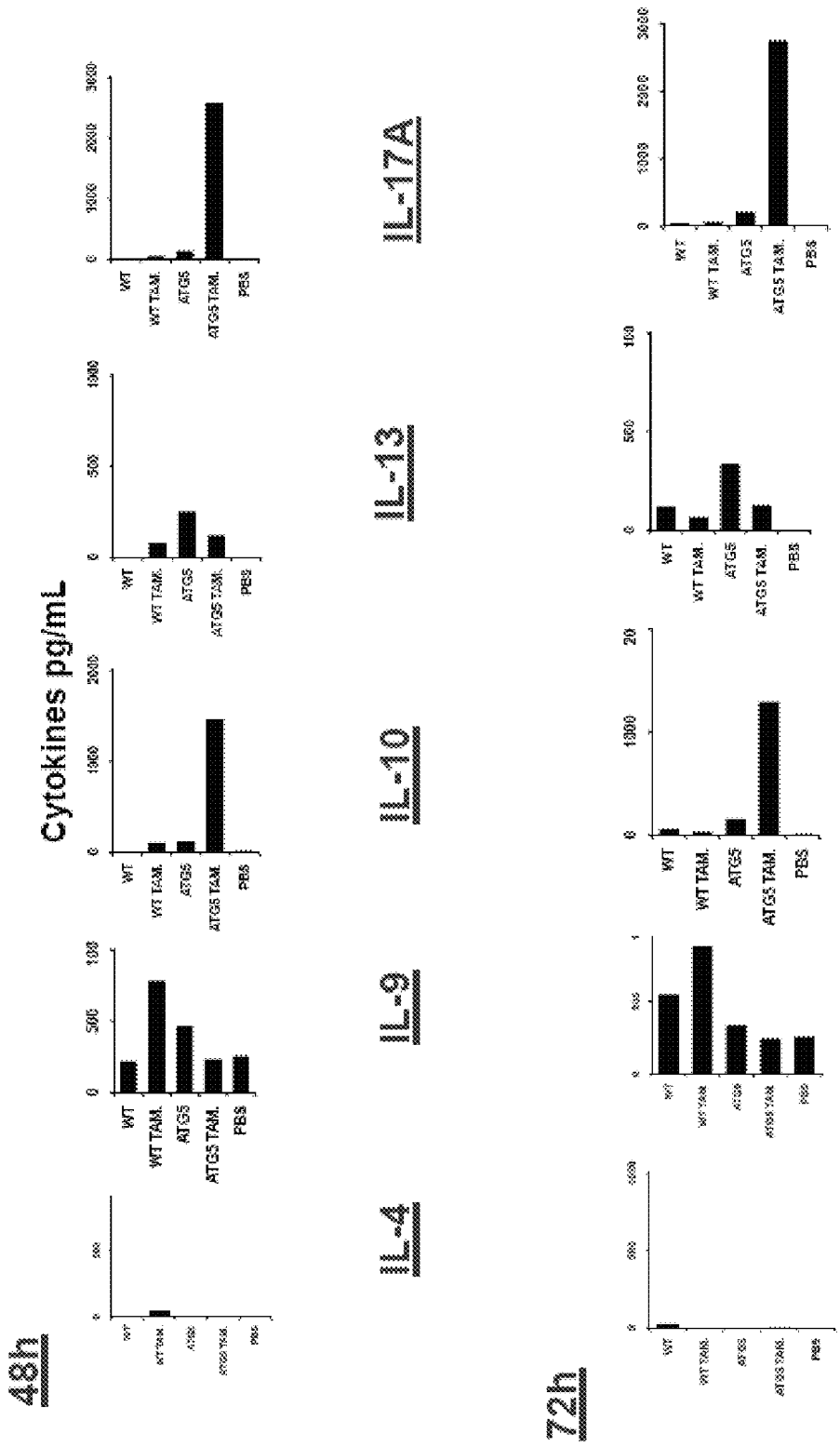

FIG. 13A illustrates a protocol to investigate pulmonary cytokine levels in conditional Atg5−/− mice treated with OVA. ATG5 gene was depleted by administration of Tamoxifen to Atg5flox/flox Ki Cre+/+ mice, and OVA were injected. CD45+lung cells from Atg−/− mice treated with OVA were purified and incubated with OVA. The concentrations of cytokines in the supernatant were measured by ELISA. FIG. 13B graphically illustrates that lack of autophagy induces IL-10 and IL-17 in the lungs. Atg5−/− mice treated with OVA exacerbate lung inflammation via cytokine production. CD45+ lung cells re-stimulated from Atg5−/− mice produce significant amount of IL-10 and IL-17A.

DETAILED DESCRIPTION OF THE DISCLOSURE

Before the compositions and methods are described, it is to be understood that the invention is not limited to the particular methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All technical and patent publications cited herein are incorporated herein by reference in their entirety. Nothing herein is to be construed as an admission that the invention is not entitled to antedate such disclosure by virtue of prior invention.

The practice of the present invention will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, $3^{rd}$ edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, $5^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; and Mayer and Walker eds. (1987) Immunochemical Methods in Cell and Molecular Biology (Academic Press, London).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above.

DEFINITIONS

As used in the specification and claims, the singular form "a", "an" and "the" include plural references unless the context clearly dictates otherwise. For example, the term "a cell" includes a plurality of cells, including mixtures thereof.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention or process steps to produce a composition or achieve an intended result. Embodiments defined by each of these transition terms are within the scope of this invention.

The term "isolated" as used herein with respect to nucleic acids, such as DNA or RNA, refers to molecules separated from other DNAs or RNAs, respectively that are present in the natural source of the macromolecule. The term "isolated peptide fragment" is meant to include peptide fragments which are not naturally occurring as fragments and would not be found in the natural state. The term "isolated" is also used herein to refer to polypeptides, antibodies, proteins, host cells and polynucleotides that are isolated from other cellular proteins or tissues and is meant to encompass both purified and recombinant polypeptides, antibodies, proteins and polynucleotides. In other embodiments, the term "isolated" means separated from constituents, cellular and otherwise, in which the cell, tissue, polynucleotide, peptide, polypeptide, protein, antibody or fragment(s) thereof, which are normally associated in nature and can include at least 80%, or alternatively at least 85%, or alternatively at least 90%, or alternatively at least 95%, or alternatively at least 98%, purified from a cell or cellular extract. For example, an isolated polynucleotide is separated from the 3' and 5' contiguous nucleotides with which it is normally associated in its native or natural environment, e.g., on the chromosome. An isolated cell, for example, is a cell that is separated form tissue or cells of dissimilar phenotype or genotype. As is apparent to those of skill in the art, a non-naturally occurring polynucleotide, peptide, polypeptide, protein, antibody or fragment(s) thereof, does not require "isolation" to distinguish it from its naturally occurring counterpart.

The term "binding" or "binds" as used herein are meant to include interactions between molecules that may be detected using, for example, a hybridization assay. The terms are also meant to include "binding" interactions between molecules. Interactions may be, for example, protein-protein, antibody-protein, protein-nucleic acid, protein-small molecule or small molecule-nucleic acid in nature. This binding can result in the formation of a "complex" comprising the interacting molecules. A "complex" refers to the binding of two or more molecules held together by covalent or non-covalent bonds, interactions or forces.

Hybridization reactions can be performed under conditions of different "stringency". In general, a low stringency hybridization reaction is carried out at about 40° C. in about 10×SSC or a solution of equivalent ionic strength/temperature. A moderate stringency hybridization is typically performed at about 50° C. in about 6×SSC, and a high stringency hybridization reaction is generally performed at about 60° C. in about 1×SSC. Hybridization reactions can also be performed under "physiological conditions" which is well known to one of skill in the art. A non-limiting example of a physiological condition is the temperature, ionic strength, pH and concentration of $Mg^{2+}$ normally found in a cell.

The term "FLIP" is conventionally defined as a FLICE-like inhibitor protein having two death effector domains, DED1 and DED2. (Thome and Tschopp (2001) Nat. Rev. Immunol. 1:50-58). As used herein, the term "cFLIP" refers to the short and long form of cellular FLIP. cFLIPs refers to the short form of cFLIP. $cFLIP_L$ refers to the long form of cFLIP. The "viral" form of FLICE-like inhibitor protein refers to viral FLIP (vFLIP) any one of Kaposi's sarcoma-associated herpesvirus (KSHV), Herpesvirus saimiri (HVS), or Molluscum contagiosum virus (MCV). As used herein, "FLIP" refers cFLIP or vFLIP. As used herein, "alpha4-TAT-vFLIP" (a.k.a. "a4-vFLIP") intends the sequence RRRQRRKKRGY-G-LMNS-FVCLIVSS (24aa) (SEQ ID No. 28, including variants and equivalents thereof.

The term "polypeptide" is used interchangeably with the term "protein" and in its broadest sense refers to a compound of two or more subunit amino acids, amino acid analogs or peptidomimetics. The subunits may be linked by peptide bonds. In another embodiment, the subunit may be linked by other bonds, e.g., ester, ether, etc. As used herein the term "amino acid" refers to natural and/or unnatural or synthetic amino acids, including glycine and both the D and L optical isomers, amino acid analogs and peptidomimetics. A peptide of three or more amino acids is commonly called an oligopeptide if the peptide chain is short. If the peptide chain is long, the peptide is commonly called a polypeptide or a protein. The term "peptide fragment" as used herein, also refers to a peptide chain.

A "hybrid peptide" between a first peptide and one or more other peptides (collectively referred to as the "original peptides") refers to a peptide having at least one amino acid identical to that of another peptide at the same position. In one aspect, a hybrid peptide includes fewer than about 60% amino acids from any of the original peptides. In one aspect, a hybrid peptide is a fusion peptide between a fragment of the first original peptide and a fragment of one of the other original peptides. In a particular aspect, the fragment is an N-terminal or a C-terminal fragment. In another aspect, a hybrid peptide is not homologous to any of the original peptides. A "hybrid peptide" of a peptide, such as an α4 FLIP peptide fragment, refers to a hybrid peptide between the peptide and one or more peptides of the same kind, such as other α4 FLIP peptide fragments.

The phrase "equivalent polypeptide" or "biologically equivalent peptide or peptide fragment" or "biologically equivalent polynucleotide" refers to a protein or a peptide fragment which is homologous to the exemplified reference polynucleotide, protein or peptide fragment and which exhibit similar biological activity in vitro or in vivo, e.g., approximately 100%, or alternatively, over 90% or alternatively over 85% or alternatively over 70%, as compared to the standard or control biological activity. Additional embodiments within the scope of this invention are identified by having more than 60%, or alternatively, more than 65%, or alternatively, more than 70%, or alternatively, more than 75%, or alternatively, more than 80%, or alternatively, more than 85%, or alternatively, more than 90%, or alternatively, more than 95%, or alternatively more than 97%, or alternatively, more than 98% or 99% sequence identity or homology. Percentage homology can be determined by sequence comparison using programs such as BLAST run under appropriate conditions. In one aspect, the program is run under default parameters.

As used herein, a variant is a peptide selected from SEQ ID NOS. 2, 4, 6 or 8, having a substitution with 1, 2, 3, or 4 amino acids at the corresponding positions of the α region of one or more other peptides selected from SEQ ID NOS. 2, 4, 6 or 8.

As understood by those of skill in the art, a "retro-inverso" refers to an isomer of a linear peptide in which the direction of the sequence is reversed ("retro") and the chirality of each amino acid residue is inverted ("inverso"). Compared to the parent peptide, a helical retro-inverso peptide can substantially retain the original spatial conformation of the side chains but has reversed peptide bonds, resulting in a retro-inverso isomer with a topology that closely resembles the parent peptide, since all peptide backbone hydrogen bond interactions are involved in maintaining the helical structure. See Jameson et al., (1994) Nature 368:744-746 (1994) and Brady et al. (1994) Nature 368:692-693. The net result of combining D-enantiomers and reverse synthesis is that the positions of carbonyl and amino groups in each amide bond are exchanged, while the position of the side-chain groups at each alpha carbon is preserved. Unless specifically stated otherwise, it is presumed that any given L-amino acid sequence of the invention may be made into an D retro-inverso peptide by synthesizing a reverse of the sequence for the corresponding native L-amino acid sequence.

The term "polynucleotide" refers to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, or EST), exons, introns, messenger RNA (mRNA), transfer RNA, ribosomal RNA, ribozymes, cDNA, RNAi, siRNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

"Homology" or "identity" or "similarity" are synonymously and refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present invention.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: http://www.ncbi.nlm.nih.gov/blast/Blast.cgi, last accessed on Nov. 26, 2007. Biologically equivalent polynucleotides are those having the specified percent homology and encoding a polypeptide having the same or similar biological activity.

The term "non-contiguous" refers to the presence of an intervening peptide, nucleotide, polypeptide or polynucleotide between a specified region and/or sequence. For example, two polypeptide sequences are non-contiguous because the two sequences are separated by a polypeptide sequences that is not homologous to either of the two sequences. Non-limiting intervening sequences are comprised of at least a single amino acid or nucleotide.

A "gene" refers to a polynucleotide containing at least one open reading frame (ORF) that is capable of encoding a particular polypeptide or protein after being transcribed and translated. Any of the polynucleotide or polypeptide sequences described herein may be used to identify larger fragments or full-length coding sequences of the gene with which they are associated. Methods of isolating larger fragment sequences are known to those of skill in the art.

The term "express" refers to the production of a gene product such as RNA or a polypeptide or protein.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in an eukaryotic cell.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced there from.

Applicants have provided herein the polypeptide and/or polynucleotide sequences for use in gene and protein transfer and expression techniques described below. It should be understood, although not always explicitly stated that the sequences provided herein can be used to provide the expression product as well as substantially identical sequences that produce a protein that has the same biological properties. These "biologically equivalent" or "biologically active" polypeptides are encoded by equivalent polynucleotides as described herein. They may possess at least 60%, or alternatively, at least 65%, or alternatively, at least 70%, or alternatively, at least 75%, or alternatively, at least 80%, or alternatively at least 85%, or alternatively at least 90%, or alternatively at least 95% or alternatively at least 98%, identical primary amino acid sequence to the reference polypeptide when compared using sequence identity methods run under default conditions. Specific polypeptide sequences are provided as examples of particular embodiments. Modifications to the sequences to amino acids with alternate amino acids that have similar charge.

A "gene delivery vehicle" is defined as any molecule that can carry inserted polynucleotides into a host cell. Examples of gene delivery vehicles are liposomes, micelles, biocompatible polymers, including natural polymers and synthetic polymers; lipoproteins; polypeptides; polysaccharides; lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

A polynucleotide of this invention can be delivered to a cell or tissue using a gene delivery vehicle. "Gene delivery," "gene transfer," "transducing," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

A "composition" is intended to mean a combination of active polypeptide, polynucleotide or antibody and another compound or composition, inert (e.g. a detectable label) or active (e.g. a gene delivery vehicle) alone or in combination with a carrier which can in one embodiment be a simple carrier like saline or pharmaceutically acceptable or a solid support as defined below.

A "pharmaceutical composition" is intended to include the combination of an active polypeptide, polynucleotide or antibody with a carrier, inert or active such as a solid support, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin (1975) Remington's Pharm. Sci., 15th Ed. (Mack Publ. Co., Easton).

A "subject," "individual" or "patient" is used interchangeably herein, and refers to a vertebrate, preferably a mammal, more preferably a human. Mammals include, but are not limited to, murines, rats, rabbits, simians, bovines, ovines, porcines, canines, felines, farm animals, sport animals, pets, equines, and primates, particularly humans.

"Cell," "host cell" or "recombinant host cell" are terms used interchangeably herein. It is understood that such terms refer not only to the particular subject cell but to the progeny or potential progeny of such a cell. The cells can be of any one or more of the type murine, rat, rabbit, simian, bovine, ovine, porcine, canine, feline, equine, and primate, particularly human. Because certain modifications may occur in succeeding generations due to either mutation or environmental influences, such progeny may not, in fact, be identical to the parent cell, but are still included within the scope of the term as used herein.

"Treating," "treatment," or "ameliorating" of a disease includes: (1) preventing the disease, i.e., causing the clinical symptoms of the disease not to develop in a patient that may be predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

The term "suffering" as it related to the term "treatment" refers to a patient or individual who has been diagnosed with or is predisposed to a disease. A patient may also be referred to being "at risk of suffering" from a disease. This patient has not yet developed characteristic disease pathology, however are know to be predisposed to the disease due to family history, being genetically predispose to developing the disease, or diagnosed with a disease or disorder that predisposes them to developing the disease to be treated.

MODES FOR CARRYING OUT THE ASPECTS OF THE DISCLOSURE

In one aspect, this disclosure provides a method for treating asthma or an associated disorder in a patient in need thereof, comprising administering to the patient an effective amount of an autophagy inducing agent, thereby treating the asthma or the associated disorder. As used herein, a "asthma associated disorder is one exhibiting clinical manifestations of an atopic, allergen-specific immune response. Non-limiting examples of asthma or associated disorders include, allergic asthma, chronic obstructive pulmonary disease, lung inflammation, respiratory tolerance and a lung infection or disorder.

For the purpose of illustration, an autophagy inducing agent is one or more of carbomezepine, tamoxifen, minoxidil, erapumil, clonidine, and an autophagy inducing FLIP peptide. For example, the autophagy inducing FLIP peptide is of the group of peptides identified by SEQ ID NO.: 1-8 or 14-28, or an equivalent thereof or a variant thereof.

Thus, in one aspect, the method is practiced using an isolated peptide fragment comprising, or alternatively consisting essentially of, or yet further consisting of, a region of the vFLIP or cFLIP protein that binds to Atg3, or a portion thereof. Examples of these fragments are identified in SEQ ID NOS. 1 through 8 or 14 through 28, including equivalents, variants or hybrids of each thereof, as well as biological equivalents of each thereof. In some aspects, the method is practiced using an isolated peptide fragment comprising, or alternatively consisting essentially of, or yet further consisting of, a region of the death effector domain (DED) of vFLIP or cFLIP, or a portion thereof. See Mol. Cell (2008) 30:262. In another aspect, the method is practiced using an isolated peptide fragment comprising, or alternatively consisting essentially of, or yet further consisting of, an alpha-helix region of a DED of vFLIP or cFLIP, or a portion thereof. In another aspect, the method is practiced using an isolated peptide fragment comprising, or alternatively consisting essentially of, or yet further consisting of, an alpha-helix region of a DED of vFLIP or cFLIP, or a portion thereof.

In another aspect, the method is practiced using an isolated peptide fragment of vFLIP comprising, or alternatively consisting essentially of, or yet further consisting of, the amino acid sequence EVVLFLLNVF (SEQ ID NO. 1) or a peptide fragment substantially homologous and biologically equivalent to SEQ ID NO. 1, a variant or hybrid thereof, or alternatively the retro-inverso form or biological equivalent of each thereof. Substantially homologous and biologically equivalent peptide fragments intend those having at least 80% homology, or alternatively at least 85% homology, or alternatively at least 90% homology, or alternatively, at least 95% homology or alternatively at least 98% homology to SEQ ID NO. 1, each as determined using methods known to those skilled in the art and identified herein, when run under default parameters. Preferred amino acid substitutions for the biologically equivalent polypeptides of SEQ ID NO. 1 are described infra.

In still another aspect, the method is practiced using an isolated peptide fragment of vFLIP that comprising, or alternatively consisting essentially of, or yet further consisting of, the amino acid sequence QTFLHWVYCMEN (SEQ ID NO. 2) or a peptide fragment substantially homologous and biologically equivalent to SEQ ID NO. 2 a variant or hybrid thereof, or alternatively the retro-inverso form or a biological equivalent of each thereof, of these peptides. Substantially homologous and biologically equivalent peptide fragments intend those having at least 80% homology, or alternatively at least 85% homology, or alternatively at least 90% homology, or alternatively, at least 95% homology or alternatively, at least 98% homology to SEQ ID NO. 2, each as determined using methods known to those skilled in the art and identified herein, when run under default parameters. Preferred amino acid substitutions for the biologically equivalent polypeptides of SEQ ID NO. 2 are described infra.

In another aspect, the method is practiced using a variant of SEQ ID NO. 2 that includes substitution with one or more amino acids at the corresponding positions of the α region of another FLIP peptide, such as but not limited to, SEQ ID NOS. 4, 6 or 8. In one aspect, the substitution with one or more amino acids is substitution with 1, or alternatively 2, or 3, or 4, or 5, or 6 amino acids from SEQ ID NO. 4, or alternatively 6, or alternatively 8, individually or in combination. In some embodiments, disclosed and provided is a hybrid peptide between SEQ ID NO. 2 and any one or more of SEQ ID NOS. 4, 6 or 8. Examples of such are shown in Table 5.

Thus, in another aspect, the method is practiced using an isolated polypeptide comprising, or alternatively consisting essentially of, or yet further consisting of, the amino acid sequence SSVILCVYCMEN (SEQ ID NO: 21) or a variant or hybrid or a peptide substantially homologous and biologically equivalent to SSVILCVYCMEN (SEQ ID NO: 21) or alternatively the retro-inverso form or a biological equivalent of each thereof. Substantially homologous and biologically equivalent peptides intend those having at least 80% homology, or alternatively at least 85% homology, or alternatively at least 90% homology, or alternatively, at least 95% homology or alternatively, at least 98% homology to SSVILCVYCMEN (SEQ ID NO: 21), each as determined using methods known to those skilled in the art and identified herein, when run under default parameters.

In another aspect, the method is practiced using an isolated polypeptide comprising, or alternatively consisting essentially of, or yet further consisting of, the amino acid sequence QTFLHWVFSNML (SEQ ID NO: 22) or a variant or hybrid or a polypeptide substantially homologous and biologically equivalent to QTFLHWVFSNML (SEQ ID NO: 22) or alternatively the retro-inverso form or a biological equivalent of each thereof. Substantially homologous and biologically equivalent peptides intend those having at least 80% homology, or alternatively at least 85% homology, or alternatively at least 90% homology, or alternatively, at least 95% homology or alternatively, at least 98% homology to QTFLHWVFSNML (SEQ ID NO: 22), each as determined using methods known to those skilled in the art and identified herein, when run under default parameters.

In another aspect, the method is practiced using an isolated polypeptide fragment comprising, or alternatively consisting essentially of, or yet further consisting of, the amino acid sequence QTFLLWVYCMEN (SEQ ID NO: 23) or a variant or hybrid or a peptide substantially homologous and biologically equivalent to QTFLLWVYCMEN (SEQ ID NO: 23) or alternatively the retro-inverso form or a biological equivalent of each thereof. Substantially homologous and biologically equivalent peptides intend those having at least 80% homology, or alternatively at least 85% homology, or alternatively at least 90% homology, or alternatively, at least 95% homology or alternatively, at least 98% homology to QTFLLWVYCMEN (SEQ ID NO: 23), each as determined using methods known to those skilled in the art and identified herein, when run under default parameters. Preferred amino acid substitutions for the biologically equivalent polypeptides of QTFLLWVYCMEN (SEQ ID NO: 23) are described herein.

In another aspect, the method uses an isolated polypeptide comprising, or alternatively consisting essentially of, or yet further consisting of, the amino acid sequence QTFLHCVYCMEN (SEQ ID NO: 24) or a variant or hybrid or a peptide substantially homologous and biologically equivalent to QTFLHCVYCMEN (SEQ ID NO: 24) or alternatively the retro-inverso form or a biological equivalent of each thereof. Substantially homologous and biologically equivalent peptides intend those having at least 80% homology, or alternatively at least 85% homology, or alternatively at least 90% homology, or alternatively, at least 95% homology or alternatively, at least 98% homology to QTFLHCVYCMEN (SEQ ID NO: 24), each as determined using methods known to those skilled in the art and identified herein, when run under default parameters. Preferred amino acid substitutions for the biologically equivalent polypeptides of QTFLHCVY-CMENSEQ ID NO: 24) are described herein.

In another aspect this invention, the method uses an isolated polypeptide comprising, or alternatively consisting essentially of, or yet further consisting of, the amino acid sequence QTFLLCVYCMEN (SEQ ID NO: 25) or a variant or hybrid or a peptide substantially homologous and biologically equivalent to QTFLLCVYCMEN (SEQ ID NO: 25) or alternatively the retro-inverso form or a biological equivalent of each thereof. Substantially homologous and biologically equivalent peptides intend those having at least 80% homology, or alternatively at least 85% homology, or alternatively at least 90% homology, or alternatively, at least 95% homology or alternatively, at least 98% homology to QTFLLCVYC-MEN (SEQ ID NO: 25), each as determined using methods known to those skilled in the art and identified herein, when run under default parameters. Preferred amino acid substitutions for the biologically equivalent polypeptides of QTFLLCVYCMEN SEQ ID NO: 25) are described herein.

In another aspect this invention, the method uses an isolated peptide comprising, or alternatively consisting essentially of, or yet further consisting of, the amino acid sequence QTFLHWVYCMMN (SEQ ID NO: 26) or a variant or hybrid or a peptide substantially homologous and biologically equivalent to QTFLHWVYCMMN (SEQ ID NO: 26) or alternatively the retro-inverso form or a biological equivalent of each thereof. Substantially homologous and biologically equivalent peptides intend those having at least 80% homology, or alternatively at least 85% homology, or alternatively at least 90% homology, or alternatively, at least 95% homology or alternatively, at least 98% homology to QTFLHWVYC-MMN (SEQ ID NO: 26), each as determined using methods known to those skilled in the art and identified herein, when run under default parameters. Preferred amino acid substitutions for the biologically equivalent polypeptides of QTFL-HWVYCMMN (SEQ ID NO: 26) are described herein.

In another aspect this invention, the method uses an isolated peptide comprising, or alternatively consisting essentially of, or yet further consisting of, the amino acid sequence QTFLLCVYCMMN (SEQ ID NO: 27) or a variant or hybrid or a peptide substantially homologous and biologically equivalent to QTFLLCVYCMMN (SEQ ID NO: 27) or alternatively the retro-inverso form or a biological equivalent of each thereof. Substantially homologous and biologically equivalent peptides intend those having at least 80% homology, or alternatively at least 85% homology, or alternatively at least 90% homology, or alternatively, at least 95% homology or alternatively, at least 98% homology to QTFLLCVYC-MMN (SEQ ID NO: 27), each as determined using methods known to those skilled in the art and identified herein, when run under default parameters. Preferred amino acid substitutions for the biologically equivalent polypeptides are described herein.

In yet another aspect, the method uses an isolated peptide fragment of cFLIP comprising, or alternatively consisting essentially of, or yet further consisting of, the amino acid sequence EMLLFLCRDV (SEQ ID NO: 3) or a variant or hybrid or a peptide fragment substantially homologous and biologically equivalent to EMLLFLCRDV (SEQ ID NO: 3) or alternatively, the retro-inverso forms or a biological equivalent of each thereof of the peptides. Substantially homologous and biologically equivalent peptide fragments intend those having at least 80% homology, or alternatively at least 85% homology, or alternatively at least 90% homology, or alternatively, at least 95% homology or alternatively, at least 98% homology to EMLLFLCRDV (SEQ ID NO: 3), each as determined using methods known to those skilled in the art and identified herein, when run under default parameters. Preferred amino acid substitutions for the biologically equivalent polypeptides of EMLLFLCRDV (SEQ ID NO: 3) are described herein.

In still another aspect, this method uses an isolated peptide fragment of cFLIP comprising, or alternatively consisting essentially of, or yet further consisting of, the amino acid sequence KSFLDLWELEK (SEQ ID NO: 4) or a variant or hybrid or a peptide fragment substantially homologous and biologically equivalent to KSFLDLVVELEKSEQ ID NO: 4) or alternatively the retro-inverso forms or a biological equivalent of each thereof of the peptides. Substantially homologous and biologically equivalent peptide fragments intend those having at least 80% homology, or alternatively at least 85% homology, or alternatively at least 90% homology, or alternatively, at least 95% homology or alternatively, at least 98% homology to KSFLDLVVELEK (SEQ ID NO: 4), each as determined using methods known to those skilled in the art and identified herein, when run under default parameters. Preferred amino acid substitutions for the biologically equivalent polypeptides of KSFLDLWELEK (SEQ ID NO: 4) are described herein.

Also for use in the methods is a variant of SEQ ID NO. 4 that includes substitution with one or more amino acids at the corresponding positions of the α region of another FLIP peptide, such as but not limited to, SEQ ID NOS. 2, 6 or 8. In one aspect, the substitution with one or more amino acids is substitution with 1, or alternatively 2, or 3, or 4, or 5, or 6 amino acids from SEQ ID NO. 2, or alternatively 6, or alternatively 8, individually or in combination. In some embodiments, the variant of SEQ ID NO. 4 is a hybrid peptide between SEQ ID NO. 4 and any one or more of SEQ ID NOS. 2, 6 or 8.

In another aspect, the method uses an isolated peptide fragment of HVS vFLIP comprising, or alternatively consisting essentially of, or yet further consisting of, the amino acid sequence YCLLFLINGC (SEQ ID NO. 5) or a variant or hybrid or a peptide fragment substantially homologous and biologically equivalent to SEQ ID NO. 5 or alternatively the retro-inverso forms or a biological equivalent of each thereof of the peptides. Substantially homologous and biologically equivalent peptide fragments intend those having at least 80% homology, or alternatively at least 85% homology, or alternatively at least 90% homology, or alternatively, at least 95% homology or alternatively, at least 98% homology to SEQ ID NO. 5, each as determined using methods known to those skilled in the art and identified herein, when run under default parameters. Preferred amino acid substitutions for the biologically equivalent polypeptides of SEQ ID NO. 5 are described herein.

In another aspect, the method uses an isolated peptide fragment of HVS vFLIP comprising, or alternatively consisting essentially of, or yet further consisting of, the amino acid sequence SSVILCVFSNML (SEQ ID NO. 6) or a variant or hybrid or a peptide fragment substantially homologous and biologically equivalent to SEQ ID NO. 6, or alternatively, the retro-inverso forms or a biological equivalent of each thereof of the peptides. Substantially homologous and biologically equivalent peptide fragments intend those having at least 80% homology, or alternatively at least 85% homology, or alternatively at least 90% homology, or alternatively, at least 95% homology or alternatively, at least 98% homology to SEQ ID NO. 6, each as determined using methods known to those skilled in the art and identified herein, when run under default parameters. Preferred amino acid substitutions for the biologically equivalent polypeptides of SEQ ID NO. 6 are described herein.

In another aspect, the method is practiced using a variant of SEQ ID NO. 6 that includes substitution with one or more amino acids at the corresponding positions of the α region of another FLIP peptide, such as but not limited to, SEQ ID NOS. 2, 4 or 8. In one aspect, the substitution with one or more amino acids is substitution with 1, or alternatively 2, or 3, or 4, or 5, or 6 amino acids from SEQ ID NO. 2, or alternatively 4, or alternatively 8, individually or in combination. In some embodiments, the variant of SEQ ID NO. 6 is a hybrid peptide between SEQ ID NO. 6 and any one or more of SEQ ID NOS. 2, 4 or 8.

In another aspect, the method uses an isolated peptide fragment of MCV MC159 comprising, or alternatively consisting essentially of, or yet further consisting of, the amino acid sequence SLLLFLCHDA (SEQ ID NO. 7) or a variant or hybrid or a peptide fragment substantially homologous and biologically equivalent to SEQ ID NO. 7 or alternatively, the retro-inverso forms or a biological equivalent of each thereof of the peptides. Substantially homologous and biologically equivalent peptide fragments intend those having at least 80% homology, or alternatively at least 85% homology, or alternatively at least 90% homology, or alternatively, at least 95% homology or alternatively, at least 98% homology to SEQ ID NO. 7, each as determined using methods known to those skilled in the art and identified herein, when run under default parameters. Preferred amino acid substitutions for the biologically equivalent polypeptides of SEQ ID NO. 7 are described herein.

In another aspect, the method uses an isolated peptide fragment of MCV MC159 comprising, or alternatively consisting essentially of, or yet further consisting of, the amino acid sequence SRFVELVLALEN (SEQ ID NO. 8) or a variant or hybrid or a peptide fragment substantially homologous and biologically equivalent to SEQ ID NO. 8 or alternatively, a retro-inverso forms or a biological equivalent of each thereof of the peptides. Substantially homologous and biologically equivalent peptide fragments intend those having at least 80% homology, or alternatively at least 85% homology, or alternatively at least 90% homology, or alternatively, at least 95% homology or alternatively, at least 98% homology to SEQ ID NO. 8, each as determined using methods known to those skilled in the art and identified herein, when run under default parameters. Preferred amino acid substitutions for the biologically equivalent polypeptides of SEQ ID NO. 8 are described herein.

In another aspect, the method uses an isolated peptide "alpha4-TAT-vFLIP" (a.k.a. "a4-vFLIP") comprising, or alternatively consisting essentially of, or yet further consisting of the sequence RRRQRRKKRGY-G-LMNSFVCLIVSS (SEQ ID No. 28), including variants and equivalents thereof including a peptide substantially homologous and biologically equivalent to SEQ ID NO. 28 or alternatively, a retro-inverso forms or a biological equivalent of each thereof of the peptides. Substantially homologous and biologically equivalent peptides intend those having at least 80% homology, or alternatively at least 85% homology, or alternatively at least 90% homology, or alternatively, at least 95% homology or alternatively, at least 98% homology to SEQ ID NO. 28, each as determined using methods known to those skilled in the art and identified herein, when run under default parameters. Preferred amino acid substitutions for the biologically equivalent polypeptides of SEQ ID NO. 28 are described herein.

Further provided for use in the methods is a variant of SEQ ID NO. 8 that includes substitution with one or more amino acids at the corresponding positions of the α region of another FLIP peptide, such as but not limited to, SEQ ID NOS. 2, 4 or 6. In one aspect, the substitution with one or more amino acids is substitution with 1, or alternatively 2, or 3, or 4, or 5, or 6 amino acids from SEQ ID NO. 2, or alternatively 4, or alternatively 6, individually or in combination. In some embodiments, a biological equivalent of SEQ ID NO. 8 is a hybrid peptide between SEQ ID NO. 8 and any one or more of SEQ ID NOS. 2, 4 or 6.

Another aspect of this invention, the method uses an isolated peptide fragment comprising, or alternatively consisting essentially of, or yet further consisting of, two non-contiguous death effector domain regions of cFLIP, wherein the regions comprise the amino acid sequences EVVLFLLNVF (SEQ ID NO. 1) and QTFLHWVYCMEN (SEQ ID NO. 2), or amino acid sequences substantially homologous and biologically equivalent to these polypeptides. Substantially homologous and biologically equivalent polypeptides intend polypeptides having at least 60%, or alternatively at least 65% homology, or alternatively at least 70% homology, or alternatively at least 75% homology, or alternatively at least 85% homology, or alternatively at least 90% homology, or alternatively, at least 95% homology or alternatively, at least 98% homology to SEQ ID NOS. 1 and 2, each as determined using methods known to those skilled in the art and identified herein, when run under default parameters. Preferred amino acid substitutions for the biologically equivalent peptides are described herein. Examples of substantially homologous and biologically equivalent to SEQ ID NO. 2, without limitation, are shown in Table 5. Also within the scope of this invention are the retro-inverso forms of these peptides.

Another aspect of this invention is a method using an isolated peptide fragment comprising, or alternatively consisting essentially of, or yet further consisting of, two non-contiguous death effector domain regions of vFLIP, wherein the regions comprise the amino acid sequences EMLLFLCRDV (SEQ ID NO. 3) and KSFLDLVVELEK (SEQ ID NO. 4), or amino acid sequences substantially homologous and biologically equivalent to these polypeptides. Substantially homologous and biologically equivalent polypeptides intend polypeptides having at least 60%, or alternatively at least 65% homology, or alternatively at least 70% homology, or alternatively at least 75% homology, or alternatively at least 85% homology, or alternatively at least 90% homology, or alternatively, at least 95% homology or alternatively, at least 98% homology to SEQ ID NOS. 3 and 4, each as determined using methods known to those skilled in the art and identified herein, when run under default parameters. Preferred amino acid substitutions for the biologically equivalent peptides are described herein. Also within the scope of this invention are the retro-inverso forms of these peptides.

Another aspect of this invention is a method using an isolated peptide fragment comprising, or alternatively consisting essentially of, or yet further consisting of, two non-contiguous death effector domain regions of HVS vFLIP, wherein the regions comprise the amino acid sequences YCLLFLINGC (SEQ ID NO. 5) and SSVILCVFSNML (SEQ ID NO. 6), or amino acid sequences substantially homologous and biologically equivalent to these polypeptides. Substantially homologous and biologically equivalent polypeptides intend polypeptides having at least 60%, or alternatively at least 65% homology, or alternatively at least 70% homology, or alternatively at least 75% homology, or alternatively at least 85% homology, or alternatively at least 90% homology, or alternatively, at least 95% homology or alternatively, at least 98% homology to SEQ ID NOS. 5 and 6, each as determined using methods known to those skilled in the art and identified herein, when run under default parameters. Preferred amino acid substitutions for the biologically equivalent peptides are described herein. Also within the scope of this invention are the retro-inverso forms of these peptides.

Another aspect of this invention, the method uses an isolated peptide fragment comprising, or alternatively consisting essentially of, or yet further consisting of, two non-contiguous death effector domain regions of MCV MC159, wherein the regions comprise the amino acid sequences SLLL-FLCHDA (SEQ ID NO. 7) and SRFVELVLALEN (SEQ ID NO. 8), or amino acid sequences substantially homologous and biologically equivalent to these polypeptides. Substantially homologous and biologically equivalent polypeptides intend polypeptides having at least 60%, or alternatively at least 65% homology, or alternatively at least 70% homology, or alternatively at least 75% homology, or alternatively at least 85% homology, or alternatively at least 90% homology, or alternatively, at least 95% homology or alternatively, at least 98% homology to SEQ ID NOS. 7 and 8, each as determined using methods known to those skilled in the art and identified herein, when run under default parameters. Preferred amino acid substitutions for the biologically equivalent peptides are described herein. Also within the scope of this invention are the retro-inverso forms of these peptides.

Further provided by this invention is the method using an isolated peptide that comprises, or alternatively consisting essentially of, or yet further consisting of, a plurality of polypeptides having two or more non-contiguous amino acid sequences as described herein, and/or or a variant or hybrid or their biological equivalents and/or the retro-inverso forms of each, examples of some which are identified herein.

Yet further provided are methods using an isolated peptide fragment having one or more polypeptides having varying degrees of sequence identity or homology to one or more of SEQ ID NOS. 1 through 8 or 14 to 28 (with, in one aspect the further limitation that amino acid 5 and/or 6 is L and/or W, respectively), e.g., at least 65% homology, or alternatively at least 70% homology, or alternatively at least 75% homology, or alternatively at least 85% homology, or alternatively at least 90% homology, or alternatively, at least 95% homology or alternatively, at least 98% homology to SEQ ID NOS. 1 through 8 or 14 through 28 (with, in one aspect the further limitation that amino acid 5 and/or 6 is L or W, respectively), each as determined using methods known to those skilled in the art and identified herein, when run under default parameters.

Yet further provided is a method as described herein using an isolated peptide fragment having one or more polypeptides having additional amino acids added onto the carboxyl-terminal end or amino-terminal end of the polypeptides of SEQ ID NOS. 1 through 8 and/or 14 through 28 such that the length of the peptide comprises an additional at least 10 amino acids, or alternatively at least 15 amino acids, or alternatively at least 20 amino acids, or alternatively at least 25 amino acids, or alternatively at least 30 amino acids, or alternatively at least 40 amino acids, or alternatively at least 50 amino acids, each amino acid added using methods known to those skilled in the art. Any of these larger peptide fragments which can in one aspect contain the contiguous amino acids as shown in the respective SEQ ID NOS. 9 through 13, be substituted in the appropriate compositions, host cells, vectors and methods as described herein. Similar to the smallest fragment shown in SEQ ID NOS. 1 through 8, this invention provides the retro-inverso form and biological equivalent forms of these larger peptide fragments. In one aspect, conjugated to the polypeptide is an amino acid that facilitates entry of the polypeptide into the cell such as the HIV TAT sequence.

It is known to those skilled in the art that modifications can be made to any peptide to provide it with altered properties. Peptide fragments of the invention can be modified to include unnatural amino acids. Thus, the peptides may comprise D-amino acids, a combination of D- and L-amino acids, and various "designer" amino acids (e.g., β-methyl amino acids, C-α-methyl amino acids, and N-α-methyl amino acids, etc.) to convey special properties to peptides. Additionally, by assigning specific amino acids at specific coupling steps, peptides with α-helices, β turns, β sheets, α-turns, and cyclic peptides can be generated. Generally, it is believed that α-helical secondary structure or random secondary structure is preferred.

It is known to those skilled in the art that modifications can be made to any peptide by substituting one or more amino acids with one or more functionally equivalent amino acids that does not alter the biological function of the peptide. In one aspect, the amino acid that is substituted by an amino acid that possesses similar intrinsic properties including, but not limited to, hydrophobic, size, or charge. Methods used to determine the appropriate amino acid to be substituted and for which amino acid are know to one of skill in the art. Non-limiting examples include empirical substitution models as described by Layoff et al. (1978) In Atlas of Protein Sequence and Structure Vol. 5 suppl. 2 (ed. MR. Day off), pp. 345-352. National Biomedical Research Foundation, Washington D.C.; PAM matrices including Day off matrices (Layoff et al. (1978), supra, or JET matrices as described by Jones et al. (1992) Compute. Appl. Basic. 8:275-282 and Gannet et al. (1992) Science 256:1443-1145; the empirical model described by Adak and Hasegawa (1996) J. Mol. Evil. 42:459-468; the block substitution matrices (BLOSSOM) as described by Henrico and Henrico (1992) Proc. Natl. Acad. Sci. USA 89:10915-10919; Poisson models as described by Neil (1987) Molecular Evolutionary Genetics. Columbia University Press, New York.; and the Maximum Likelihood (ML) Method as described by Muller et al. (2002) Mol. Biol. Evil. 19:8-13.

Accordingly, in yet another aspect the isolated peptide fragment may comprise, or alternatively consisting essentially of, or yet further consisting of, a "biologically equivalent" or "biologically active" peptide fragment encoded by equivalent polynucleotides as described herein. They may possess at least 60%, or alternatively, at least 65%, or alternatively, at least 70%, or alternatively, at least 75%, or alternatively, at least 80%, or alternatively at least 85%, or alternatively at least 90%, or alternatively at least 95% or alternatively at least 98%, identical primary amino acid sequence to the reference polypeptide when compared using sequence identity methods run under default conditions. For example, one or more of the valise, isoleucine, leucine, methionine, phenylalanine, or tryptophan residues of the hydrophobic core of an alpha helix of a death effector domain may be modified or substituted with another hydrophobic residue such as valine, isoleucine, leucine, methionine, phenylalanine, or tryptophan. In some embodiments, one or more of the valine, isoleucine, leucine, methionine, phenylalanine, or tryptophan residues of the amino acid sequences of SEQ ID NO. 1, SEQ ID NO. 2, SEQ ID NO. 3, SEQ ID NO. 4, SEQ ID NO. 5, SEQ ID NO. 6, SEQ ID NO. 7, or SEQ ID NO. 8, etc., may be modified or substituted with another hydrophobic residue such as valine, isoleucine, leucine, methionine, phenylalanine, or tryptophan.

Proteins and peptide fragments comprising, or alternatively consisting essentially of, or yet further consisting of, the amino acid sequences of the invention can be prepared by expressing polynucleotides encoding the polypeptide sequences of this invention in an appropriate host cell. This can be accomplished by methods of recombinant DNA technology known to those skilled in the art. Accordingly, this invention also provides methods for recombinantly producing the polypeptides of this invention in a eukaryotic or prokaryotic host cell, which in one aspect is further isolated from the host cell. The proteins and peptide fragments of this invention also can be obtained by chemical synthesis using a commercially available automated peptide synthesizer such as those manufactured by Perkin Elmer/Applied Biosystems, Inc., Model 430A or 431A, Foster City, Calif., USA. The synthesized protein or polypeptide can be precipitated and further purified, for example by high performance liquid chromatography (HPLC). Accordingly, this invention also provides a process for chemically synthesizing the proteins of this invention by providing the sequence of the protein and reagents, such as amino acids and enzymes and linking together the amino acids in the proper orientation and linear sequence.

The protein and peptide fragments may be operatively linked to a transduction domain for facilitated cell entry. Protein transduction offers an alternative to gene therapy for the delivery of therapeutic proteins into target cells, and methods involving protein transduction are within the scope of the invention. Protein transduction is the internalization of proteins into a host cell from the external environment. The internalization process relies on a protein or peptide which is able to penetrate the cell membrane. To confer this ability on a normally non-transducing protein, the non-transducing protein can be fused to a transduction-mediating protein such as the antennapedia peptide, the HIV TAT protein transduction domain, or the herpes simplex virus VP22 protein. See Ford et al. (2001) Gene Ther. 8:1-4. As such the polypeptides of the invention can, for example, include modifications that can increase such attributes as stability, half-life, ability to enter cells and aid in administration, e.g., in vivo administration of the polypeptides of the invention. For example, polypeptides of the invention can comprise, or alternatively consisting essentially of, or yet further consisting of, a protein transduction domain of the HIV TAT protein as described in Schwarze, et al. (1999) Science 285:1569-1572, and exemplified below.

In a further aspect, any of the proteins or peptides of this invention can be combined with a detectable label such as a dye for ease of detection.

This invention also provides pharmaceutical composition for in vitro and in vivo use in the methods as disclosed herein, the compositions comprising, or alternatively consisting essentially of, or yet further consisting of a therapeutically effective amount of the FLIP peptide fragment that causes at least about 75%, or alternatively at least about 80%, or alternatively at least about 85%, or alternatively at least about 90%, or alternatively at least about 95%, or alternatively at least about 99% effectiveness in the methods provided herein when applied in a molar concentration of less than about 10 micromolar, or alternatively less than about 9 micromolar, or alternatively less than about 8 micromolar, or alternatively less than about 7 micromolar, or alternatively less than about 6 micromolar, or alternatively less than about 5 micromolar, or alternatively less than about 4 micromolar, or alternatively less than about 3 micromolar, or alternatively less than about 2 micromolar, or alternatively less than about 1 micromolar, or alternatively less than about 0.5 micromolar, or alternatively less than about 0.25 micromolar concentration, as compared to a control that does not receive the composition. Comparative effectiveness can be determined by suitable in vitro or in vivo methods as known in the art and described herein.

In one aspect, the method is practiced using a peptide coded by a polynucleotide that hybridizes to the coding or non-coding strand of a polypeptide that encodes peptides identified by SEQ ID NO.: 1-8 or 14-28 under conditions of moderate or high stringency.

In any of the above methods, the patient is a mammal such as a human patient.

Administration of the autophagy inducing agent(s) can be by local or systemic administration. Details of modes of administration are described below.

Also provided is a transgenic mouse defective in Atg5 protein function, that can be used for screening a compound or agent for the ability to treat asthma or a related disorder comprising administering to the mouse a candidate agent for an effective amount of time, and assaying for improved lung function, wherein if the mouse has improved lung function, the compound or agent is a candidate for the treatment of asthma or a related disorder.

For the purpose of illustration only, the asthma is allergic asthma or the related disorder is one or more of chronic obstructive pulmonary disease, lung inflammation, respiratory tolerance and a lung infection or disorder. The response can be compared to response of a known autophagy inducing agent, e.g., one or more of carbomezepine, tamoxifen, minoxidil, erapumil, clonidine, and an autophagy inducing FLIP peptide.

As used herein, an "effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents of the present invention for any particular subject depends upon a variety of factors including the activity of the specific compound employed, the age, body weight, general health, sex, and diet of the subject, the time of administration, the rate of excretion, the drug combination, and the severity of the particular disorder being treated and form of administration. Treatment dosages generally may be titrated to optimize safety and efficacy. Typically, dosage-effect relationships from in vitro and/or in vivo tests initially can provide useful guidance on the proper doses for patient administration. In general, one will desire to administer an amount of the peptide fragment, polypeptide, polynucleotide, antibody, or compositions of this invention to increase autophagy either in vitro or in vivo by at least 10%, 25%, 40%, 60%, 80%, 90% or 95% as compared to control. Determination of these parameters is well within the skill of the art. These considerations, as well as effective formulations and administration procedures are well known in the art and are described in standard textbooks.

The "therapeutically effective amount" will vary depending on the peptide fragment, polypeptide, polynucleotide, or compositions, the disease and its severity and the age, weight, etc., of the patient to be treated all of which is within the skill of the attending clinician.

Administration in vivo can be effected in one dose, continuously or intermittently throughout the course of treatment. Methods of determining the most effective means and dosage of administration are well known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents can be found below.

The pharmaceutical compositions can be administered orally, intranasally, parenterally, intravenously, topically, or by inhalation therapy, and may take the form of tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition to an agent of the present invention, the pharmaceutical compositions can also contain other pharmaceutically active compounds or a plurality of compounds of the invention.

More particularly, an agent of the present invention also referred to herein as the active ingredient, may be administered for therapy by any suitable route including oral, rectal, nasal, topical (including transdermal, aerosol, buccal and sublingual), vaginal, parenteral (including subcutaneous, intramuscular, intravenous and intradermal) and pulmonary. It will also be appreciated that the preferred route will vary with the condition and age of the recipient, and the disease being treated.

Ideally, the agent should be administered to achieve peak concentrations of the active agent at sites of disease. This may be achieved, for example, by the intravenous injection of the agent, optionally in saline, or orally administered, for example, as a tablet, capsule or syrup containing the active ingredient. Desirable blood levels of the agent may be maintained by a continuous infusion to provide a therapeutic amount of the active ingredient within disease tissue. The use of operative combinations is contemplated to provide therapeutic combinations requiring a lower total dosage of each component agent than may be required when each individual therapeutic compound or drug is used alone, thereby reducing adverse effects.

While it is possible for the agent to be administered alone, it is preferable to present it as a pharmaceutical formulation comprising at least one active ingredient, as defined above, together with one or more pharmaceutically acceptable carriers therefor and optionally other therapeutic agents. Each carrier must be "acceptable" in the sense of being compatible with the other ingredients of the formulation and not injurious to the patient.

Formulations include those suitable for oral, rectal, nasal, topical (including transdermal, buccal and sublingual), vaginal, parenteral (including subcutaneous, intramuscular, intravenous and intradermal) and pulmonary administration. The formulations may conveniently be presented in unit dosage form and may be prepared by any methods well known in the art of pharmacy. Such methods include the step of bringing into association the active ingredient with the carrier that constitutes one or more accessory ingredients. In general, the formulations are prepared by uniformly and intimately bringing into association the active ingredient with liquid carriers or finely divided solid carriers or both, and then if necessary shaping the product.

Formulations of the present invention suitable for oral administration may be presented as discrete units such as capsules, cachets or tablets, each containing a predetermined amount of the active ingredient; as a powder or granules; as a solution or suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations suitable for nasal administration, wherein the carrier is a solid, include a coarse powder having a particle size, for example, in the range of about 20 to about 500 microns which is administered as a dry powder or in an inhaler device by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the agent.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies.

The following examples are intended to illustrate, and not limit, the inventions disclosed herein.

EXPERIMENTAL

Experiment No. 1

Autophagy is a highly conserved cellular process present in all eukaryotes that is essential for survival (Yang et al. (2009) Curr Top Microbiol Immunol 335:1-32; Yang et al. (2010) Nat Cell Biol 12:814-822). Once autophagy has been initiated (by starvation or some other stimulus) an expanding membrane, known as the isolation membrane, is generated that engulfs components of the cytosol including organelles such as the mitochondria. This membrane eventually fuses to generate a structure know as the autophagosome, which subsequently fuses with lysosomes to form an autolysosome (Yang et al. (2009) Curr Top Microbiol Immunol 335:1-32; Yang et al. (2010) Nat Cell Biol 12:814-822). The formation of the autolysosome results in breakdown of the contents of the autophagosomes by the enzymes introduced from the lysosome. The resulting products from autolysosome degradation can be recycled into new components of the cell. Alternatively, if the cell is an antigen-presenting cell the output from the autolysosome may be loaded onto antigen presenting molecules to activate the immune system or alternatively can activate pattern recognition receptors (Deretic et al. (2009) Cell Host Microbe 5:527-549; Lee et al. (2010) Immunity 32:227-239; Paludan et al. (2005) Science 307: 593-596; Jounai et al. (2007) Proc Natl Acad Sci USA 104: 14050-14055; Lee et al. (2007) Science 315:1398-1401; Levine (2011) Nature 469:323-335).

Applicant has generated two different transgenic mouse lines wherein Atg5, a gene essential for autophagy, is deleted using the cre-loxP method. Atg5 can be deleted in the whole body using an inducible (rosa26 cre ERT) cre recombinase. Alternatively, Atg5 can be specifically deleted using a tissue specific promoter, surfactant protein c (sftpc), resulting in deletion throughout the lung (Williams et al. (2008) Nat Chem Biol 4:295-305; Zhang et al. (2007) Proc Natl Acad Sci USA 104:19023-19028; Fleming et al. (2011) Nat Chem Biol 7:9-17). These two models enable the evaluation of the contribution of local and systemic autophagy in the development of asthma.

Evidence suggests that numerous FDA-approved therapeutics used in the treatment of other conditions can also influence autophagy. These include compositions used to treat seizures (e.g. carbamazepine which has previously been shown to improve asthma by an unknown mechanism (16)), depression (e.g. DCMI a metabolite of clomipramine) and hypertension (e.g. minoxidil, verapamil, clonidine) (Renna et al. (2010) J Biol Chem 285:11061-11067; Balgi et al. (2009) PLoS One 4:e7124; Mizushima et al. (2006) Autophagy 2:302-304; Vooijs et al. (2001) EMBO Rep 2:292-297). In addition there is much interest in the design and development of more specific modulators of autophagy (Fujita et al. (2008) Mol Biol Cell 19:2092-2100; Kuma et al. (2004) Nature 432:1032-1036; Inoue et al. (2011) Biochem Biophys Res Commun 405:13-18).

This experiment shows how autophagy affects the development of airway hyperreactivity (AHR) and cytokine production by T cells. Applicant has obtained Atg5flox/flox mice on the C57B16/J background (Okubo et al. (2005) Development 132:1363-1374), from Dr Jae Jung of the University of Southern California, and have crossed the Atg5flox/flox to mice expressing cre recombinase ubiquitously under the control of the estrogen receptor, which can be specifically activated by tamoxifen (rosa26 Cre ERT (Hadeiba et al. (2003) J Immunol 170:5502-5510)). Atg5 is an essential protein for autophagy, which forms a complex with Atg12 and Atg16L and is responsible for the elongation of the isolation membrane (Korfhagen et al. (1990) Proc Natl Acad Sci USA 87:6122-6126). In accordance with this essential role, Atg5 knockout mice die shortly after birth due to an inability to survive post-partum starvation (Akbari et al. (2010) Mucosal Immunol 3:81-91).

Figures 1A, 1B, 1C:
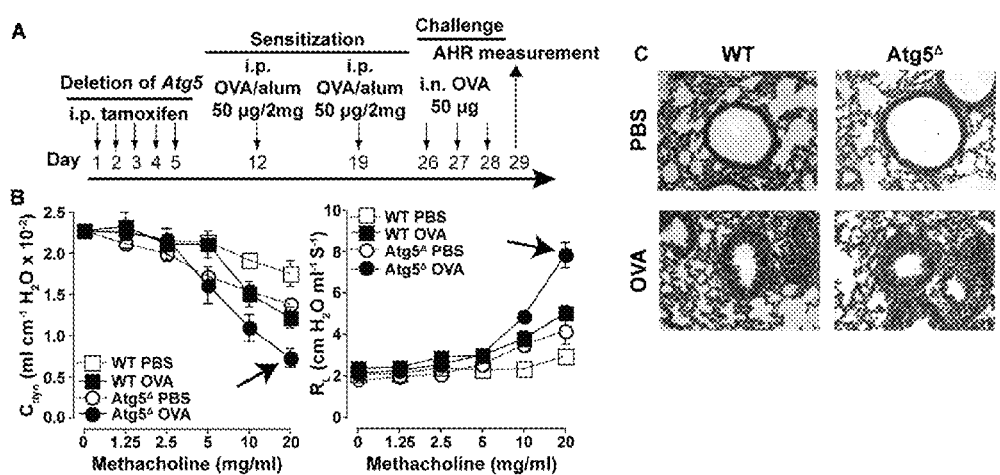
FIGS. 1A to 1C show increased airway hyperreactivity ("AHR") and lung inflammation in Atg5Δ mice (a transgenic mouse wherein Atg5, a gene essential for autophagy, has been deleted) after respiratory exposure to allergen ovalbumin ("OVA").

Using the Atg5flox/flox rosa26Cre ERT mouse line, Applicant has successfully generated Atg5 deletion with five intraperitoneal (i.p.) doses of tamoxifen, a regime that has been determined to result in >90% deletion of Atg5 in the lung and spleen by quantitative PCR (Q-PCR). Groups of animals were sensitized and challenged with allergen (ovalbumin ("OVA") protein, FIG. 1A). Deletion of Atg5 (Atg5Δ) results in increased airway resistance and decreased dynamic compliance after intranasal (i.n.) allergen challenge (FIG. 1B). Lung histology indicates enhanced cellular infiltration and airway thickening (hematoxylin and eosin (H&E) staining) in Atg5Δ mice after exposure to OVA corroborating the increased AHR in these animals (FIG. 1C). These results suggest that genetic blockade of autophagy greatly increases AHR in response to allergen. Interestingly, very recently it has been reported that deletion of Atg7 in airway epithelial cells increases lung resistance (Lombardi et al. (2010) J Immunol 184:2107-2115).

Stated another way, and referring to FIG. 1, this figure shows increased AHR and lung inflammation in Atg5Δ. mice after respiratory exposure to OVA. In FIG. 1A, the scheme for deletion of Atg5 and induction of AHR is indicated. FIG. 1B shows that AHR was determined by invasive plethysmography and is expressed as lung resistance (RL, right) and dynamic compliance (Cdyn, left) for C57B16/J (WT) or Atg5flox/flox rosa26Cre ERT after deletion by tamoxifen i.p. (Atg5Δ). FIG. 1C shows representative lung histopathology images after sections have been stained with H&E. Intraperitoneal (i.p.), intranasal (i.n.), representative data from two experiments, mean±SEM with 4 mice per group.

A lung specific Atg5 deficient model using the sftpc promoter can be generated. Expression via the sftpc promoter early in embryogenesis will result in the specific deletion of Atg5 and therefore autophagy in epithelial cells of diverse cell types of the lung, including ciliated and nonciliated columnar cells of the bronchi and bronchioles, and type II and type I cells of the alveolar region (Fleming et al. (2011) Nat Chem Biol 7:9-17). This promoter has been widely used by many groups to investigate the effect of lung specific deletion or expression of proteins (Williams et al. (2008) Nat Chem Biol 4:295-305; Zhang et al. (2007) Proc Natl Acad Sci USA 104:19023-19028; Fleming et al. (2011) Nat Chem Biol 7:9-17). This approach allows determination if the aforementioned observations are due to blockade of autophagy in cells of the immune system versus local within the lung microenvironment by comparing the results from these two knockout models. In all cases, a small sample of lung tissue and lymph node and spleen can be collected for the Q-PCR determination of Atg5 expression in order to check the effectiveness of the cre deletion. AHR can be induced using the protocol above (FIG. 1A without tamoxifen for sftpc-cre) and animals are then subjected to invasive plethysmography where mice are anesthetized, tracheostomized and AHR is determined by exposing the airways to increasing doses of nebulized methacholine with 21 parameters recorded including lung resistance and dynamic compliance. In addition, lungs from a subset of animals can be harvested and prepared for histological analysis of lung inflammation, airway remodeling and mucus production. The resulting slides are stained with periodic acid Schiff stain (PAS, for carbohydrates in the mucus) or H&E (for structure and inflammatory cell infiltrates).

Stained sections are analyzed in a blinded fashion to allow for unbiased interpretation. Alternatively, lungs will be subjected to collagenase/DNase digestion and percoll gradient centrifugation for the isolation of lymphocytes. These lymphocytes are analyzed by multi-color flow cytometry (8-color BD FACS Canto II) to determine the identity and phenotype of the cells (CD4/8 T, NKT, NK, B, DC and macrophage). Finally BAL fluid is collected for the enumeration of immune cell infiltration by generating cytospin preparations and diff-quick staining as reported previously (Stock et al. (2009) J Immunol 182:5116-5122; Bursch et al. (1996) Carcinogenesis 17:1595-1607; Harris et al. (2007) Immunity 27:505-517).

In addition, a murine model of asthma has been generated using the more clinically relevant allergen, house dust mite (HDM), which has been established by Applicant based on prior studies from other groups (Gutierrez et al. (2004) Cell 119:753-766; Pyo et al. (2005) J Biol Chem 280:20722-20729). With this model, more severe AHR, lung inflammation and airway remodeling is observed. Standardized lysate of HDM is commercially available from Greer laboratories and administered intranasally on 3 consecutive days for 2 weeks at a dose of 25 µg (FIG. 2). Lung inflammation and AHR will be determined one day after the last dose of HDM.

These studies are useful to show the crucial role for autophagy in lung function and the development of AHR. A well-established breeding colony of the Atg5flox/flox rosa26Cre ERT mice can be established, and the sftpc-cre mice can be crossed to the Atg5flox/flox animals to generate complete knockouts. Invasive plethysmography on anesthetized and tracheostomized animals can be achieved using Buxco equipment as described previously (Stock et al. (2009) J Immunol 182:5116-5122; Bursch et al. (1996) Carcinogenesis 17:1595-1607; Harris et al. (2007) Immunity 27:505-517).

One caveat to using a tamoxifen inducible cre recombinase is that it has previously been shown that tamoxifen can induce autophagy. Without being bound by theory, before the deletion of Atg5, an increased autophagic flux may be generated, however, Applicant believes that the delay (>7 days) between tamoxifen administration and antigen sensitization and challenge in the methods should negate this possible contradiction. It is possible that blocking autophagy before the sensitization procedure may not allow for the development of immune responses due to alterations in antigen presentation. Although, Applicant previously demonstrated successful initiation of AHR in the OVA sensitized and challenged Atg5 deleted mice, confirmation of these findings using small molecule inhibitors of autophagy is possible.

Moreover, after induction of AHR, T cells from the lungs and draining lymph nodes can be isolated to perform in vitro restimulation with titrating doses of OVA. T cell proliferation after OVA restimulation can be determined by 3H thymidine incorporation and IL-2 production in the supernatant by ELISA. These studies can be performed in both Atg5flox/flox rosa26Cre ERT mice and Atg5flox/flox sftpc-cre mice and compared to control mice (Wild type (WT), WT treated with tamoxifen and Atg5flox/flox rosa26Cre ERT not treated with tamoxifen). The results from these studies can serve to address the contribution of local deletion of Atg5 in the lungs versus systemic deletion of Atg5 to the development of AHR.

Experiment No. 2

This experiment can determine if administration of autophagy inhibitors or inducers affect AHR development.

Figures 3A, 3B, 3C, 3D, 3E:
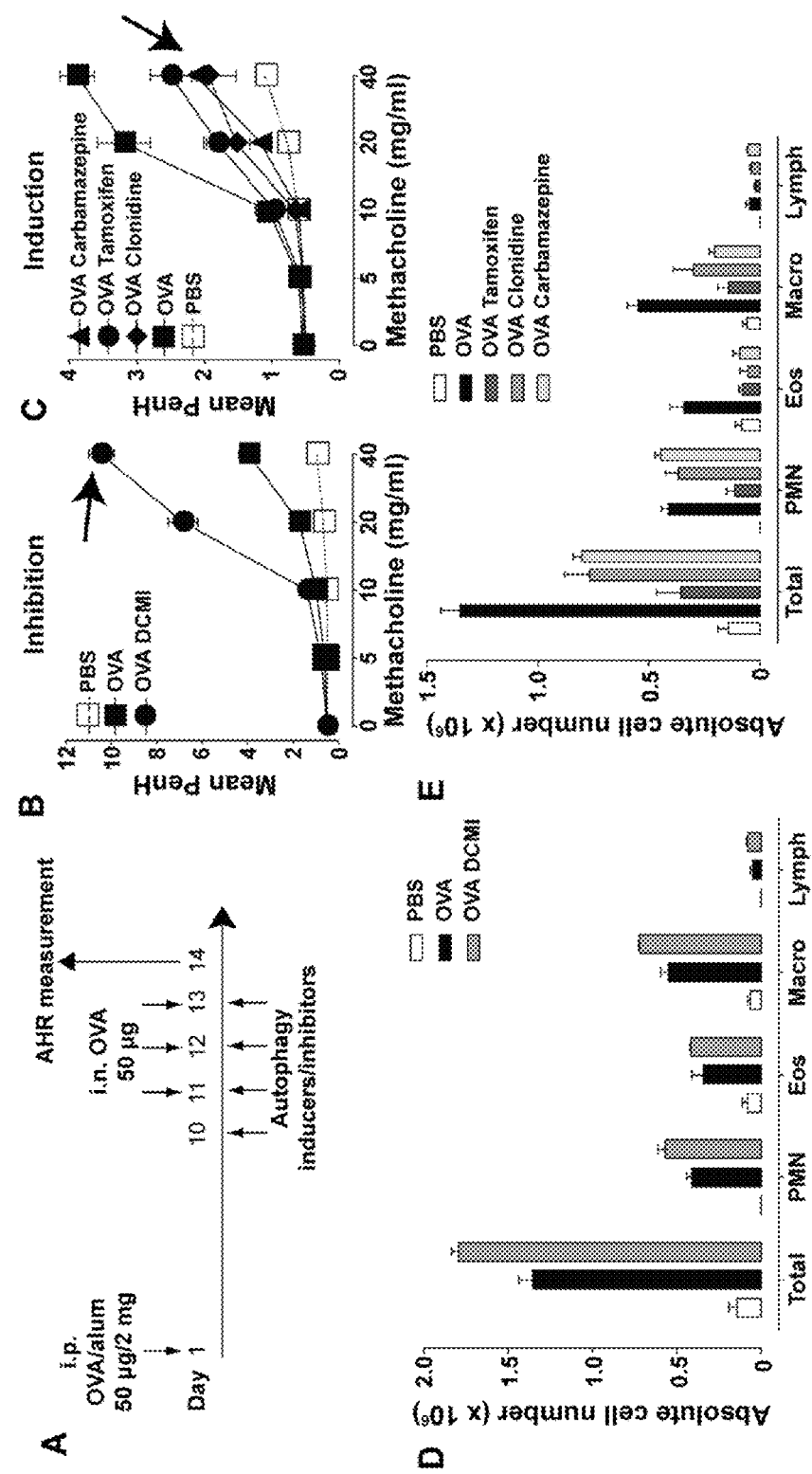
FIGS. 3A to 3E illustrate altered development of AHR and lung inflammation in BALB/c mice treated with autophagy inducers and inhibitor.

There are many reported small molecule inducers and inhibitors of autophagy (Balgi et al. (2009) PLoS One 4:e7124; Mizushima et al. (2006) Autophagy 2:302-304; Vooijs et al. (2001) EMBO Rep 2:292-297; Fujita et al. (2008) Mol Biol Cell 19:2092-2100; Kuma et al. (2004) Nature 432:1032-1036; Inoue et al. (2011) Biochem Biophys Res Commun 405:13-18). In preliminary studies, Applicant has used a range of different inducers (tamoxifen (Akbari et al. (2001) Nat Immunol 2:725-731), clonidine (Mizushima et al. (2006) Autophagy 2:302-304) and carbamazepine (Renna et al. (2010) J Biol Chem 285:11061-11067)) and one inhibitor (desmethylclomipramine ("DCMI") (Balgi et al. (2009) PLoS One 4:e7124)). A standard sensitization and challenge protocol was used for the induction of AHR in BALB/c (FIG. 3A). When autophagy was inhibited (with DCMI) AHR after sensitization and challenge with OVA was greatly increased compared to controls (FIG. 3B). This is in agreement with Applicant's findings using the Atg5Δ animals that inhibition of autophagy has a deleterious effect on lung function. When autophagy is induced (with tamoxifen, clonidine or carbamazepine) AHR after sensitization and challenge with OVA is reduced compared to controls (FIG. 3C). These findings are corroborated by the degree of cellular infiltration into the BAL and hence lung inflammation. When autophagy is inhibited total cell numbers in the BAL are increased (FIG. 3D) in contrast, in the presence of autophagy inducers total cell numbers and in particular eosinophils are reduced (FIG. 3E).

Experiment No. 3

Figures 2A, 2B, 2C:
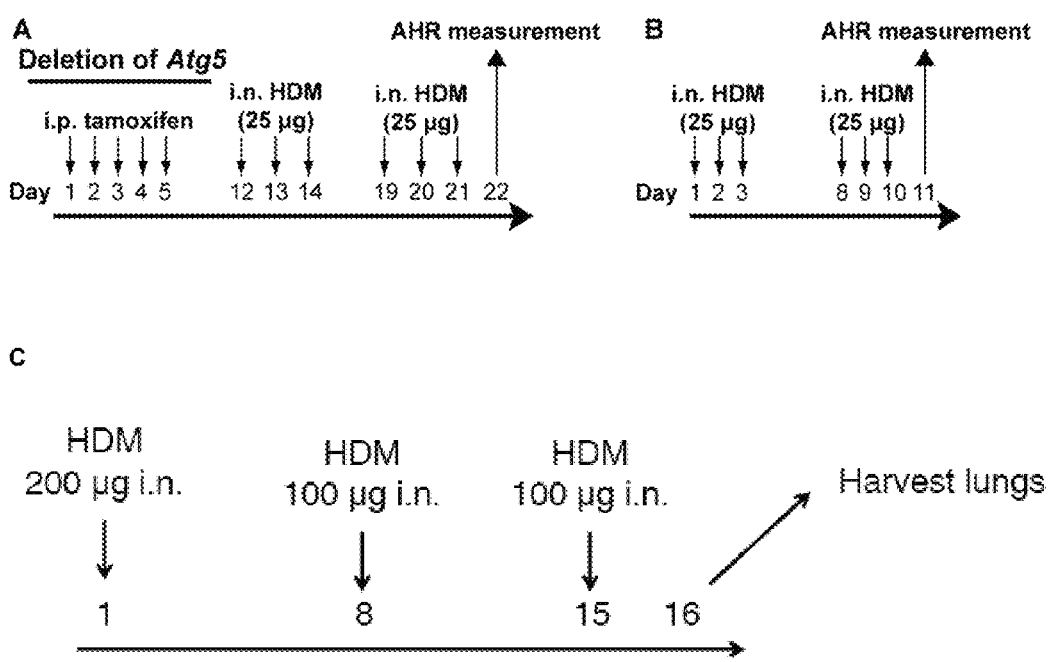
FIGS. 2A to 2C show the experimental protocol for house dust mite ("HDM") induced AHR.
Figure 4:
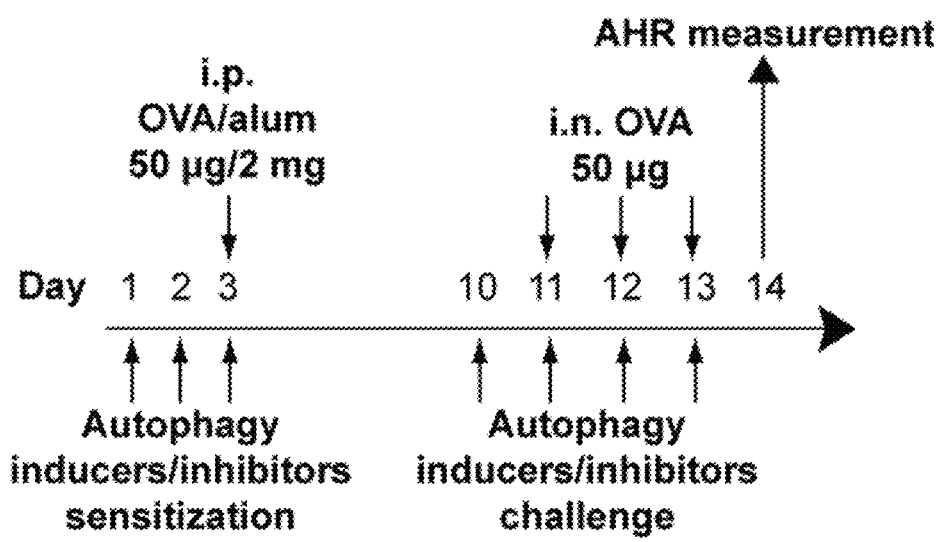
FIG. 4 shows two different administration procedures that can be used to determine at what stage in the development of AHR alteration to autophagy has the greatest effect. The autophagy modifiers can either be administered during sensitization and challenge or alternatively during respiratory challenge.

The prior finding can be extended with the compounds outlined above and include other known autophagy inducers such as minoxidil and verapamil and autophagy inhibitors/blocker such as 3-methyladenine, bafilomycin, chloroquine and wortmannin (Balgi et al. (2009) PLoS One 4:e7124; Mizushima et al. (2006) Autophagy 2:302-304; Vooijs et al. (2001) EMBO Rep 2:292-297; Fujita et al. (2008) Mol Biol Cell 19:2092-2100; Kuma et al. (2004) Nature 432:1032-1036; Inoue et al. (2011) Biochem Biophys Res Commun 405:13-18). Two different administration procedures can be used to determine at what stage in the development of AHR alteration to autophagy has the greatest effect. The autophagy modifiers can either be administered during sensitization and challenge or alternatively during respiratory challenge (FIG. 4). FIG. 2C illustrates the protocol to induce asthma in BALB/c mice by HDM. As Applicant uses the BALB/c strain, AHR can be determined by whole body plethysmography (as in FIGS. 3B and C) with these findings confirmed by performing invasive plethysmography (lung resistance and dynamic compliance) upon increasing doses of methacholine. An essential control experiment was used to quantify the effect of the compounds on autophagy by performing western blot analysis on a portion of lung tissue. The tissue was homogenized in lysis buffer in the presence of protease inhibitors and protein content determined by Bradford assay. Protein samples were separated by SDS-PAGE and transferred to PVDF membranes. The resulting blots were probed with anti-LC3 antibodies and anti-p62 antibodies. Blots were normalized with anti-β-actin antibodies. LC3 is processed during the autophagic process and is converted from a cytosolic form (LC3-I) to a phosphatidylethanolamine conjugated membrane bound version (LC3-II). The relative proportion of LC3-I and LC3-II indicates the number of autophagosomes. However, if autophagosome and lysosome fusion is impaired or lysosome function is blocked, LC3-II is not degraded and will still be increased even though autophagy is blocked. Therefore determining the degradation of autophagy substrates (such as p62) can assist in the assignment of whether autophagy is actually decreased (increased p62/decreased LC3-II) or blocked (increased p62/increased LC3-II) (Akbari et al. (2002) Nat Med 8:1024-1032). FIG. 4B shows the western blot for the expression of p62, LC3-1 and LC3-11. Higher levels in the lungs of HDM treated group with AHR strongly suggests that autophagy pathway is severely impaired.

These pre clinical experiments can determine autophagy levels in human epithelial cells after treatment with autophagy inhibitors and inducers and determine the compounds which demonstrate the greatest efficacy at a biochemical level (immunoblot results) and functional level (reduction of AHR and BAL infiltration). Success of the development of antigen specific T cell responses by IL-2 production by ELISA and 3H thymidine incorporation can be determined after in vitro restimulation with antigen using T cells isolated from the draining lymph nodes and lungs as described above. In addition, BAL fluid can be harvested for determination of infiltrating immune cells and lungs can be harvested (from animals not subjected to invasive plethysmography) for histological analysis of immune cell infiltration, airway remodeling and mucus production as described above.

Without being bound by theory, Applicant expects to extend the findings and further define the pharmacological agents that have the greatest effect on autophagic flux in vivo. In addition, Applicant anticipates that inhibitors of autophagy will exacerbate AHR and lung inflammation and with the corollary that inducers will reduce disease severity. However, many of these compounds have effects on other aspects of cellular function and in the development of an immune response in addition to their effects on autophagy. Therefore, in order to indicate specificity it is necessary to use multiple agents to inhibit and induce autophagy and demonstrate the same effect on asthma parameters (AHR and lung inflammation). The choice of pharmacological agents is also important and the most effective compounds target multiple and distinct part of the autophagy pathway. By performing the immunoblot studies, compounds can be identified that have the greatest efficacy in vivo to induce or inhibit autophagy. Correlating the biochemical studies with the functional determination of AHR and lung inflammation can focus on three inducers to take forward in future studies. In addition by performing titration studies with these compounds, Applicant can determine the effective dose that can be used in translational human studies.

Experiment No. 4

As an alternative approach, the HDM model of asthma can be used, which although it will involve the same protocols and procedures, represents the next step toward eventual clinical translation with the use of a complex and clinically highly relevant mixture of allergenic proteins.

In one aspect, 25 μg of HDM is administered on 3 consecutive days per week for two weeks (See FIG. 2b). During the second week, Applicant will also administer the autophagy inducers and inhibitors starting one day before HDM and every day during HDM i.n. This murine model of asthma results in an enhanced severity of AHR and also other relevant clinical features such as airway remodeling. Therefore, it represents a better model for the clinical setting and a more realistic validation of the potential use of autophagy inducers as therapeutic intervention in models of established AHR.

A separated protocol was developed by Applicant and is illustrated in FIG. 2C.

Experiment No. 5

This experiment can determine if alterations to autophagy can lead to differential cytokine secretion and in turn result in the polarization of immune responses.

From previous studies it is evident that alterations to the autophagy pathway can result in defective T cell responses. For example, dendritic cells (DCs) lacking autophagy (by genetic or chemical means) have defective priming of CD4+ T cells and defective TH1 responses following viral infection (Lee et al. (2010) Immunity 32:227-239) although the effect on TH2 responses was not described. Modulation of autophagy can be tested to alter TH polarization and the cytokines released after T cell activation.

The first requirement for a functional autophagy pathway in the in vitro polarization of naïve CD4+ TH cells into TH1, TH2 and TH17 cells. To assess this requirement, OVA specific naïve CD4+ TH cells are purified from the spleen of DO11.10 Rag−/− mice by AutoMACS using the clonotypic TCR antibody KJ1.26. These purified cells ($1 \times 10^5$) are co-cultured with bone marrow derived DCs pulsed with 1 μg/ml OVA peptide ($2 \times 10^4$) in the presence of the conditions for polarization. These conditions include for TH2 (IL-4 and anti-IL-12), TH1 (IFN-γ, IL-12 and anti-IL-4) and TH17 (TGF-β, IL-6, IL-23, IL-1, anti-IFN-γ and anti-IL-4) (46). At 42, 66 and 90 hours a fraction of the cells are removed and restimulated with phorbol myristate acetate (PMA, 20 ng/ml) and ionomycin (1 nM) in medium containing monensin or brefeldin. After 4 to 6 hours, the cells are stained and processed for intracellular cytokine staining to determine the percentage of cells expressing IL-4 (TH2), IFN-γ (TH1) and IL-17 (TH17) to determine the degree of TH polarization. Isotype control antibodies are used to determine the positive gates. These in vitro tests can be performed in the presence of autophagy inhibitors and inducers. In order to test the in vivo polarization, whole body or lung specific Atg5 deficient mice outlined above are sensitized and challenged with OVA or HDM. In addition, mice treated with the pharmacological autophagy inhibitors and inducers are used. Single cell suspensions from spleen, draining lymph nodes and lungs can be prepared by methods known in the art, e.g., collagenase digestion and the cells will be subjected to restimulation with PMA and ionomycin as outlined above. Alternatively, T cell restimulation can be performed in vitro with the antigens (OVA or HDM) and harvest supernatant for cytokine analysis by ELISA. Of particular interest will be if there is an alteration to the bias of the immune response when autophagy is genetically blocked by the deletion of Atg5 or blocked by chemical treatments. To determine this, a range of TH1 cytokines (IFN-γ, IL-2 and TNF-α), TH2 cytokines (IL-4, IL-5, IL-9 and IL-13) and TH17 cytokine (IL-17) can be measured, e.g., by ELISA or as the percentage of cytokine positive cells by intracellular staining.

Applicant anticipates that these studies will indicate that inhibition of autophagy will result in enhanced TH2 type cytokines or alternatively decreased TH1 cytokines. This can result in a negative feedback loop as TH2 cytokines can inhibit autophagy. Because antigen specific T cells are rare in the draining lymph nodes and lung it may not be possible to determine cytokine secretion from these cells ex vivo by ELISA or intracellular staining. As an alternative approach Applicant can isolate these antigen specific cells by flow cytometry using our BD FACSAria III and subject the sorted cells to complete cytokine analysis by Q-PCR. Alternatively, the expression of the genes involved in TH subset differentiation including GATA-3 (TH2), T-bet (TH1) and RORγt (TH17) can be measured. As it has been previously demonstrated that Atg5−/− DCs cannot support the development of TH1 cell after viral infection, it is possible that some of the effects observed are due to failures in antigen presentation or some other effect on the antigen presenting cells rather than on the T cells themselves. To dissect the contribution, WT DCs and antigen presenting cells for Atg5−/− T cells can be used. Alternatively, Atg5−/− or naïve CD4+ T cells from BALB/c spleens can be activated in the presence of chemical autophagy inhibitors/inducers using an antigen presenting cell free system. Here T cells can be activated with plate bound anti-CD3 and soluble anti-CD28 (both at 2 μg/ml) in the presence of the optimal polarization conditions outline above, and TH polarization can be determined by intracellular cytokine staining as described above. Using the combination of these methods, the effects dysregulation of autophagy has on TH polarization and subsequent cytokine release can be dissected. This will provide key information regarding if a decrease in autophagic flux is a contributing factor to the TH2 polarization seen in allergic asthma patients and provide clues to the therapeutic potential for autophagy inducers in correcting this defect in vivo.

Experiment No. 6

This experiment is designed to elucidate the role of autophagy in the abrogation of respiratory tolerance. When any particle enters the lungs there are two possible outcomes either the development of an immune response or blockade in the generation of an immune response. This blockade in the generation of an immune response in the airways is known as respiratory tolerance and occurs in non-allergic individuals upon inhalation of pollen and other non-hazardous particles. This balance between induction of an immune response and tolerance needs to be carefully balanced to prevent aberrant activation and the subsequent development of allergic asthma or insufficient response and delayed clearance of an infection. Tolerance is achieved by altering antigen specific T cells (either by clonal deletion, functional anergy or by suppression via regulatory T cells) and can also be mediated by DCs (through cytokine secretion or cell-contact dependant mechanisms). Applicant has previously demonstrated that a breakdown in respiratory tolerance underlies the development of TH2 biased immune responses and the subsequent development of AHR (Lucian et al. (2010) Nat Cell Biol 12:863-875; de Heer et al. (2004) J Exp Med 200:89-98; Nedjic et al. (2008) Nature 455:396-400; Hori et al. (2003) Science 299: 1057-1061; Fontenot et al. (2005) Immunity 22:329-341). However, several mechanisms may be responsible for the breakdown of respiratory tolerance and in the development of AHR.

Experiment No. 7

This experiment can determine if induction or inhibition of autophagy alter the development of respiratory tolerance.

Applicant has previously demonstrated that intranasal exposure to antigen leads to the development of antigen specific T cell tolerance that is in part dependant on tolerogenic DCs (de Heer et al. (2004) J Exp Med 200:89-98), IL-10 producing regulatory T (Treg) cells expressing Foxp3+ (Nedjic et al. (2008) Nature 455:396-400; Fontenot et al. (2005) Immunity 22:329-341).

Figures 5A, 5B:
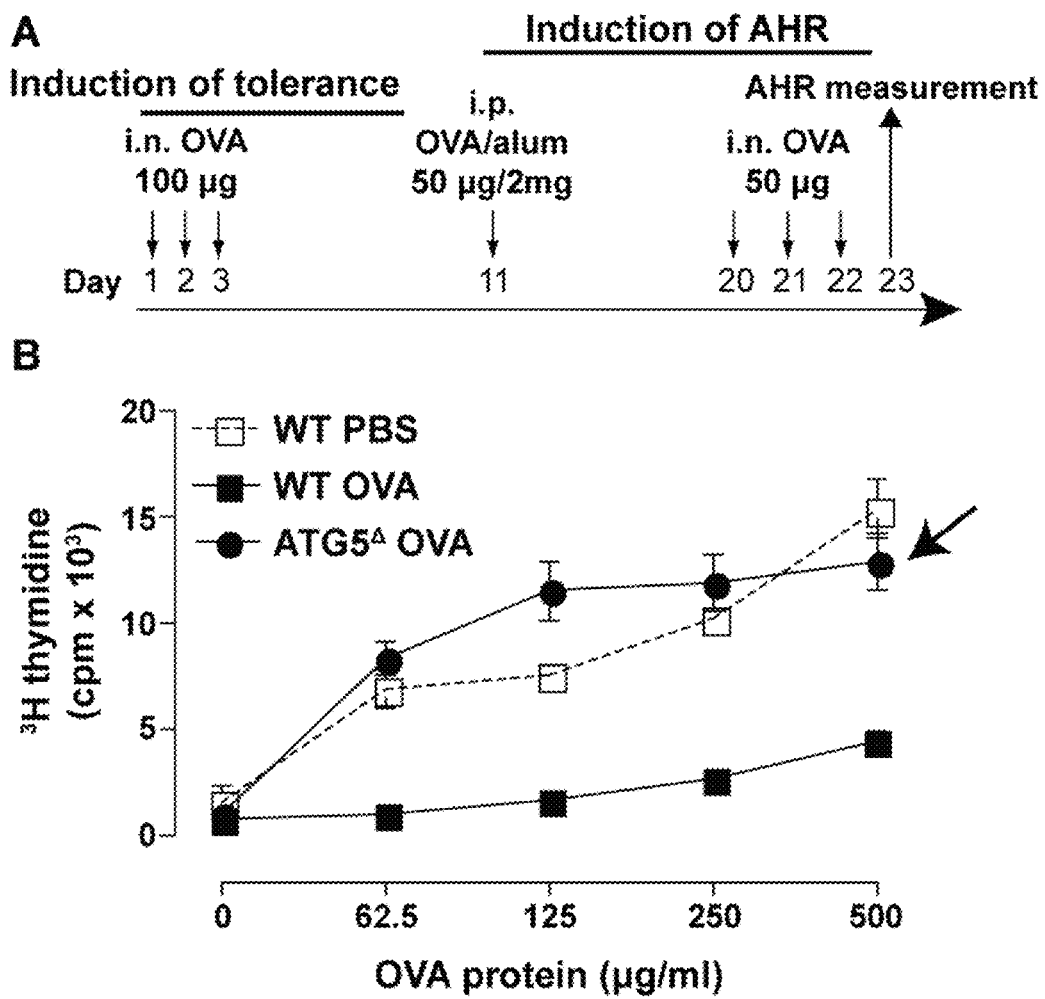
FIGS. 5A and 5B show abrogation of tolerance in Atg5Δ mice.

Using the Atg5flox/flox rosa26Cre ERT mice, Applicant tested the role of autophagy in the induction of tolerance after exposure to respiratory antigen. Atg5Δ mice were prepared as previously indicated (FIG. 1A) and were then subjected to the induction of tolerance with i.n. administration of OVA as indicated in FIG. 5A. After sensitization with i.p OVA/alum spleens were harvested to test for the induction of T cell tolerance. Splenocytes were prepared and restimulated in vitro with a titrating dose of OVA. In agreement with Applicant's previous findings (de Heer et al. (2004) J Exp Med 200:89-98; Nedjic et al. (2008) Nature 455:396-400), WT mice that had received OVA i.n. developed T cell tolerance to OVA as demonstrated by the decreased T cell proliferation in response to OVA restimulation (WT OVA FIG. 5B). In contrast, WT mice that did not receive OVA i.n demonstrated robust proliferation to stimulation with OVA (WT PBS, FIG. 5B). These results suggest that a functional autophagy pathway is required for the development of T cell tolerance in response to respiratory exposure to antigen.

Using our standard procedure for induction of respiratory tolerance as indicated in FIG. 5A above, the whole body or lung specific Atg5 deficient mouse models are used to probe the link between autophagy and the development of respiratory tolerance. By using the two models blockade of autophagy can be tested if blockage solely in the lungs is sufficient to prevent the induction of tolerance or if other cell types are involved. To test if alterations to autophagy result in the defective establishment of respiratory tolerance, AHR can be tested after sensitization and challenge with OVA by invasive plethysmography. The degree of airway inflammation can be investigated by lung histology (H&E and PAS staining), FACS analysis of lung lymphocytes and cellular components of BAL as described above. In other studies the development of T cell tolerance can be tested after the induction of respiratory tolerance. In this protocol, tolerance is induced by three i.n. challenges with OVA. After sensitization with OVA/alum i.p. spleen and draining lymph node is collected from the animals and used for in vitro assessment of T cell tolerance by measurement of T cell proliferation after in vitro restimulation with OVA according to standard methods.

The correct regulation of the autophagy pathway is required for the development of respiratory tolerance and a lack of autophagy prevents respiratory tolerance. Without being bound by theory, Applicant believes that deficiency of autophagy only in the cells of the lungs is sufficient to cause this effect. As an alternative approach, the use of chemical autophagy inhibitors can confirm that functional autophagy pathway is essential for tolerance to be induced. With the inducers, it is possible that tolerance can be enhanced and compounds that demonstrate this effect will be of particular interest for clinical translation. It is possible that administration of the autophagy inducers/inhibitors can affect T cell responses in general; therefore, it will be helpful to perform all possible permutations in the protocols to definitively prove that it is tolerance that is affected rather than a non-specific effect on the generation of OVA T cell responses.

Experiment No. 8

This experiment tests if autophagy affects the number or function of pulmonary tolerogenic DCs. Pulmonary DCs play a vital role in the control of immune responses, they acquire inhaled particles and after migrating to the bronchiole lymph nodes process and present particle components to the CD4+ T cell repertoire. Critical roles for tolerogenic conventional DCs (de Heer et al. (2004) J Exp Med 200:89-98) and plasmacytoid DCs (Battaglia et al. (2005) Blood 105:4743-4748) have been suggested in the development of respiratory tolerance. How this interaction between DC and T cell leads to the development of an immune response or tolerance is not understood. Without being bound by theory, Applicant hypothesizes that it may be associated with the antigen repertoire that can be presented and thus can be modulated by autophagy.

Using the whole body or lung specific Atg5 deficient models, tolerance can be induced with three intranasal doses of OVA on consecutive days. Lungs and draining lymph nodes are harvested 24 hours after the last OVA i.n. as this is the timepoint where Applicant previously demonstrated the highest frequency of tolerogenic DCs are present in the draining lymph nodes (de Heer et al. (2004) J Exp Med 200:89-98). To isolate DCs from the lung tissue and draining lymph nodes, they will be subjected to collagenase/DNase digestion according to standard protocols and the lymphocytes from the lungs purified by percoll gradient centrifugation. The frequency and phenotype (co-stimulatory and inhibitory receptor expression) of the various DC subsets will be determined by multicolor FACS analysis for conventional DCs (CD11chigh) and plasmacytoid DCs (mPDCA1+ CD11cdim). In addition, cytokine production (IL-10 and IL-12) can be tested by the DCs after activation with anti-CD40 antibody. This can be tested by any method known to the skilled artisan, e.g., either by intracellular cytokine staining, ELISA or Q-PCR after sorting DC subpopulations with FACSAria III. The antigen presentation function of the DCs are tested first by determining the uptake of fluorescent antigen (allophycocyanin-OVA) using a time course FACS experiment. Either total cells or purified DCs are placed in culture medium (RPMI 1640 10% FBS) at either 37° C. (to allow antigen uptake) or at 4° C. (no endocytosis can occur to detect non specific staining) and samples removed every 15 min for FACS analysis of the fluorescence intensity of allo-phycocyanin-OVA in DCs. Next the actual ability of the DCs to present antigens and activate T cells is tested in co-culture experiments. Purified DCs (either total CD11c+ isolated by magnetic microbeads and autoMACS or DC subsets sorted using FACSAria III, $2\times10^4$ cells per well) are pulsed with full length OVA protein (100 μg/ml) and cultured with OVA-TCR transgenic T cells (CD4+ cells isolated from DO11.10 Rag−/− spleens, $1\times10^5$ cells per well). Proliferation of T cells is tested by 3H thymidine incorporation and IL-2 secretion in the supernatants by ELISA after 72 hours. Activation of T cells can also be tested by cell surface upregulation of CD69 and CD25 on the T cells by FACS.

Without being bound by theory, Applicant expects to find that blockade of autophagy breaks tolerance by affecting the phenotype and/or function of pulmonary tolerogenic DCs. Using two different autophagy deficient models, Applicant can determine in what cell types autophagy is required for the induction of tolerogenic DCs. Autophagy may be required in part for the generation of peptides for antigen presentation and as a result causes defective priming of T cells when blocked as previously demonstrated (Lee et al. (2010) Immunity 32:227-239). As Applicant has previously demonstrated, adoptive transfer of these tolerogenic DCs is sufficient to induce tolerance in naïve animals, as an alternative approach, Applicant will isolate the WT and Atg5Δ DCs on day 4 from the lungs and adoptively transfer ($2\times10^5$ cells) into naïve animals. The recipients can then be tested for tolerance as indicated above and Applicant has demonstrated before (de Heer et al. (2004) J Exp Med 200:89-98).

Experiment No. 9

This experiment will test if lack of autophagy alters the development of regulatory T cells.

The autophagic machinery is required for the correct development of a self-tolerant T cell repertoire. This is because autophagy is essential for the generation of peptides in the thymic epithelial cells for negative selection during thymic T cell development (Mizushima et al. (2010) Cell 140:313-326). Regulatory T cells (Treg) including those defined by the transcription factor Foxp3 are critically important for the control of autoimmune disorders (Hori et al. (2003) Science 299:1057-1061; Ziegler (2006) Annu Rev Immunol 24:209-226). These Treg cells can either be naturally occurring or induced by the conversion of naïve T cells in the presence of TGF-β. In addition Applicant has demonstrated that Foxp3+ Treg cells in the lungs are important for the development and maintenance of respiratory tolerance (Fontenot et al. (2005) Immunity 22:329-341). Therefore, the link between alterations to autophagy and the development and function of Foxp3+ Treg cells is investigated.

As it has been demonstrated previously that autophagy is required for the correct development of a self-tolerant T cell repertoire in the thymus, Applicant will first determine the outcome of autophagy blockade on natural Foxp3+ Treg (nTreg) cells using an inducible Atg5 deficient model. Once mice have reached immunological maturity (6 to 8 weeks of age) Atg5 will be deleted as described herein. The frequency of nTreg cells can be determined in thymus, spleen, lymph node and lung after intracellular staining for Foxp3. These results will determine the role of autophagy in maintaining the nTreg repertoire. Next Applicant will test the requirement for autophagy in the induction of Tregs (iTreg), which Applicant has shown to be increased in the lungs of animals after the induction of respiratory tolerance (Nedjic et al. (2008) Nature 455:396-400; Fontenot et al. (2005) Immunity 22:329-341). Atg5 is deleted in mature animals and then respiratory tolerance is induced by three consecutive intranasal doses of OVA. Lungs, draining lymph node and spleen are harvested 24 hours after the last OVA dose and the frequency of Foxp3+ cells can be determined by flow cytometry. In order to discriminate between natural and induced Tregs, the marker Helios is used, which was demonstrated to allow the discrimination these subsets of cells (Thornton et al. (2010) J Immunol 184:3433-3441). Alternatively, programmed death 1 (PD-1) can be used as a specific marker of natural Foxp3+ Tregs (A. Y. Rudensky, Keystone symposia). Cytokine secretion by Tregs can be determined by intracellular staining after in vitro restimulation with PMA and ionomycin in the presence of brefeldin A.

In order to be able to test the function of Tregs, the Foxp3eGFP mouse (Fontenot et al. (2005) Immunity 22:329-341) can be used, which Applicant has backcrossed onto the BALB/c background. During the induction of tolerance, autophagy inducers or inhibitors are administered. Lungs and draining lymph nodes are harvested and the frequency of Foxp3eGFP+ T cells will be determined by flow cytometry. Another important function that will be tested is the ability of the Treg cells to suppress T cell proliferation after activation. This is the major advantage of using the Foxp3eGFP model as it allows rapid and specific purification of viable Treg cells by flow cytometry (CD4+ CD25+ Foxp3eGFP+) and use of these cells for subsequent in vitro assays. DO11.10 CD4+ T cells will be used ($8\times10^4$ cells) activated with bone marrow derived DCs pulsed with 1 μg/ml OVA peptide ($2\times10^4$ cells, generated by the culture of bone marrow with GM-CSF) in a standard dye dilution assay using Cell Trace™ violet or far red (Invitrogen). Suppression of T cell proliferation is tested by adding the purified Treg cells at different suppressor to responder ratios (1:1, 1:2, 1:4, 1:8, 1:16 and 1:32) and analyzing the proliferation by FACS after 4 days.

Applicant expects that when autophagy is inhibited after development of the T cell repertoire the frequency of nTregs will be normal. In contrast, Applicant anticipates that when autophagy is blocked iTreg cells cannot be induced in response to inflammatory conditions and therefore this is one reason why tolerance does not develop. It has previously been shown that rapamycin, an autophagy inducer, can increase the number of Tregs (Battaglia et al. (2005) Blood 105:4743-

4748). Therefore, to rule out effects of chemical compounds that are independent of autophagy, pharmacological inducers or inhibitors are used in vitro to test their ability to affect Treg induction. Here, an antigen presenting cell independent protocol is used to define the direct effect of these compounds on T cell conversion. Purified CD4+ T cells from Foxp3eGFP spleens are cultured in the presence of plate bound anti-CD3 and soluble anti-CD28 (both at 2 μg/ml) with or without the addition of TGF-β (1 ng/ml). Foxp3eGFP expression can be determined by any appropriate method, e.g., by flow cytometry on days 3 to 6. Foxp3eGFP animals can be crossed to ATG5flox/flox rosa26Cre ERT animals in order to be able to perform subsequent assays on Foxp3+ sorted cells which is not possible if using intracellular staining to determine Foxp3 expression as that requires fixation and permeabilization of the cells. An alternative to the FACS based assay for the suppression of proliferation is to measure 3H thymidine incorporation in the presence of γ-irradiated antigen presenting cells and IL-2 production in the supernatant by ELISA.

Experiment No. 10

Applicant can determine if regulation of autophagy is defective in patients with asthma compared to controls and test if there is a correlation between the severity of asthma and the defect in autophagy. Compounds that have shown efficacy in pre-clinical studies can be tested to determine if they will exhibit the same effects on patient derived samples. This will provide a complete pre-clinical set of data to allow for the future design of clinical trials into the therapeutic use of these compounds.

Experiment No. 11

Figure 6:
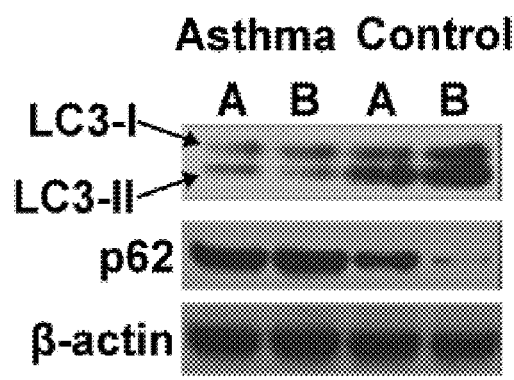
FIG. 6 shows decreased autophagy in human lung samples from severe asthma patients. Immunoblot analysis of autophagy in lung biopsy samples from two patients with severe persistent asthma and two controls. Representative images of immunoblots probed with antibodies against LC3, p62 and β-actin.

This experiment will determine autophagic flux and expression of autophagy related genes in samples from patients with moderate to severe persistent asthma. Applicant has analyzed the autophagic flux in lung biopsy samples from severe asthma patients and controls, which can support the hypothesis regarding the role of dysregulated autophagy in the development of asthma. Applicant has performed immunoblotting for the two forms of LC3 (LC3-I and LC3-II) along with an autophagy substrate (p62) and β-actin to normalize the data. As can be seen in FIG. 6, LC3-I levels are not altered dramatically between the groups however, there is a striking decrease in the amount of LC3-II in the severe asthma patients compared to controls. Along with the increased amount of p62 in these severe asthma patients, this would indicate that autophagy in human patients with severe asthma is decreased. This is to our knowledge the first time that any defect in autophagy has been demonstrated in human asthma patients.

Clinical samples from asthma patients or controls are obtained that meet criteria for inclusion lung biopsy samples and BAL will be collected by bronchoscopy. In addition, peripheral blood is drawn from the same patients (60 ml). BAL fluid and peripheral blood from moderate to severe persistent asthma patients is subjected to sorting by flow cytometry (BD FACS Aria III). T cells (CD3+ CD45+), macrophages/monocytes (CD45+ CD14+) and epithelial cells (CD45−) will be isolated. The cells are washed with saline solution and lysed in the presence of protease inhibitors and protein content measured by the Bradford assay. In addition our clinical collaborators can provide lung biopsy samples that Applicant will homogenized in radioimmuno precipitation assay buffer in the presence of protease inhibitors to generate protein lysates and protein content can be determined by a known method, e.g., by Bradford assay. Protein samples will be separated by SDS-PAGE and transferred to PVDF membranes. The resulting blots will be probed with anti-LC3 antibodies and anti-p62 antibodies. Blots will be normalized with anti-β-actin antibodies (see example of analysis in FIG. 6 above). The relative proportion of LC3-I and LC3-II indicates the number of autophagosomes and is determined by performing densitometry analysis on the blot images. However, if autophagosome and lysosome fusion is impaired or lysosome function is blocked LC3-II is not degraded and will still be increased even though autophagy is blocked. Therefore determining the degradation of autophagy substrates (such as p62) will assist in the measurement of autophagic flux. There are three possible outcomes from this analysis; increased p62 and decreased LC3-II indicating decreased autophagy; decreased p62 and increased LC3-II indicating increased autophagy or increased p62 and increased LC3-II indicating a block in autophagy/lysosomal degradation. The results from asthma patients will be compared to normal individuals and using clinical parameter information provided by a clinician, such as FEV1, Applicant will address if there is any correlation between the severity of asthma and the degree of dysfunction in autophagic flux as defined by immunoblot analysis.

Applicant provides this complete determination to confirm the preliminary studies and will indicate that regulation of autophagy is defective in asthma patients. The protocols, reagents and controls for the analysis of autophagic flux have been established by Dr Jae U. Jung. There are caveats with all methods to measuring a dynamic process such as autophagy using static measurements such as immunoblotting (Akbari et al. (2002) Nat Med 8:1024-1032). However, when using freshly isolated patient samples is not possible to take advantage of LC3-GFP or LC3-GFP-RFP fusion proteins which have been so useful in cell lines for live imaging of autophagy (Akbari et al. (2002) Nat Med 8:1024-1032). An alternative approach is to perform immunofluorescence staining of LC3 on fixed cell preparations. In this case diffuse staining (indicating LC3-I in the cytosol) and punctate staining (showing LC3-II on autophagosome membranes) can be quantified. In addition the use of a lysosomal protein marker (LAMP1 or LAMP2) can help in the determination of which structures are autophagosomes (LC3 positive only) versus autophagolysosomes (LC3 and LAMP1/2 positive) and provide and estimate on potential autophagic flux. A further test can be to perform Q-PCR analysis of the expression of autophagy genes in the human samples. Generally it is not considered that autophagy is regulated at the transcriptional level due to the essential housekeeping function it performs for cellular survival. However, to rule out any alterations to gene expression in asthma patients Applicant will check the expression of ATG5, ATG7, ATG12, LC3 and ATG16L in the samples from asthma patients and compare to controls. Also with human samples there is the inherent genetic variability that is not observed when using in-bred mouse lines which necessitates greatly increased number of samples in order to be able to have power in the analysis. Dr. Richard Barbers and his clinical staff can obtain on average samples from 24 severe or moderate asthma patients per year and 12 appropriate control subjects.

Experiment No. 12

Figures 7A, 7B:
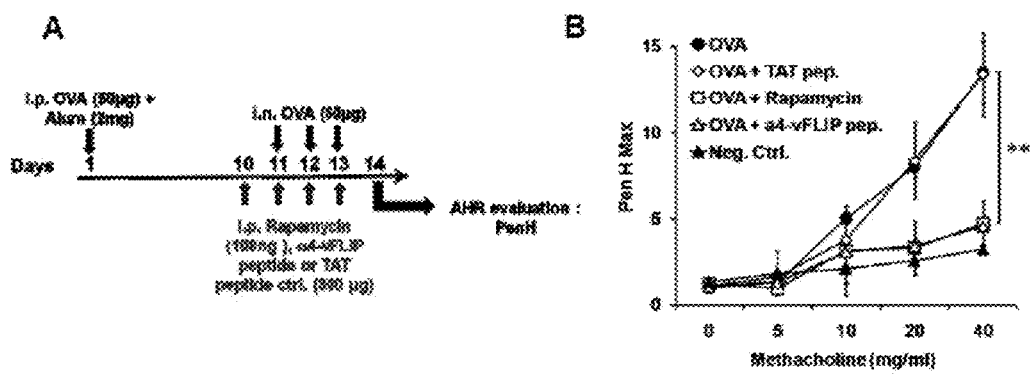
FIGS. 7A and 7B show the effect of authophagy inducers on AHR.
Figure 8A:
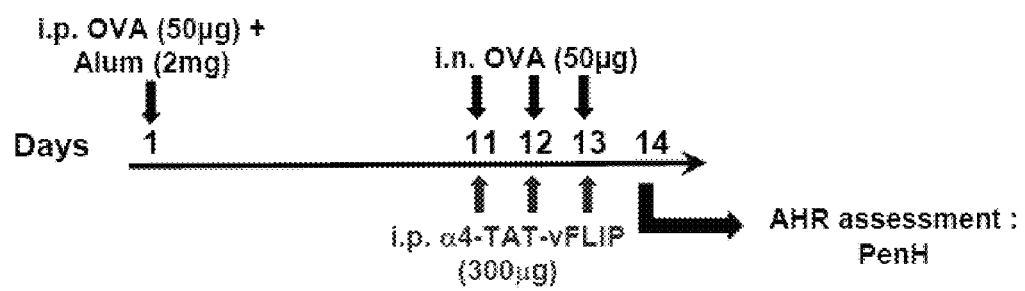
FIG. 8A shows the protocol to induce acute AHR by ovalbumin (OVA) administration. Briefly on day 1, naïve BALB/c mice (N=5 per group) received an intraperitoneal (i.p.) injection with ovalbumin (OVA) (50 m) in Alum (2 mg). After resting for 10 days, mice were treated intranasally (i.n.) with OVA (50 μg) and i.p. with the autophagy inducer α4-TAT-vFLIP (300 m) on days 11 to 13. On day 14, the enhanced pause (PenH) variable was measured to determine airway hyperreactivity (AHR).
Figure 8B:
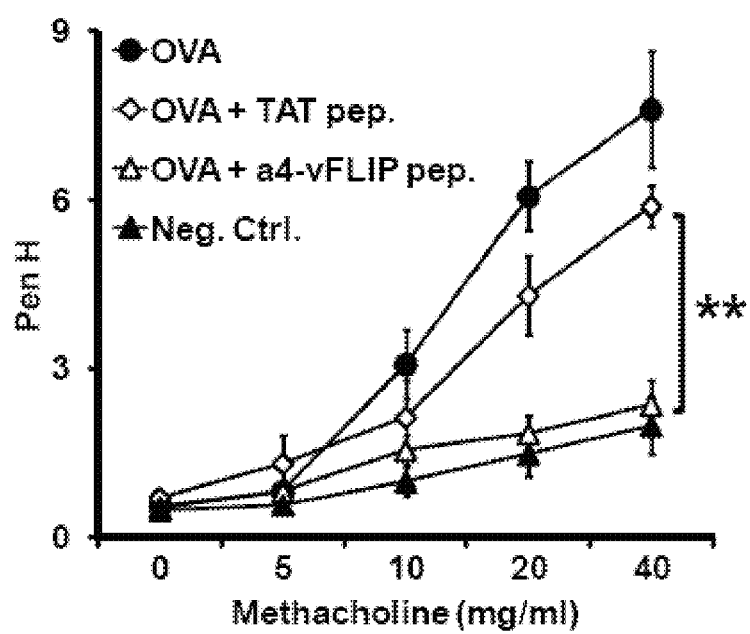
FIG. 8B shows the results of this study. Briefly, administration of alpha4-TAT-vFLIP (a.k.a. a4-vFLIP) peptide restores lung function in an acute model of OVA induced asthma. Increasing doses of methacholine, a muscarinic receptor agonist to induce AHR, was administered to the different treatment groups of mice and the PenH was determined. OVA (dark circles) treated mice exhibited increased AHR compared to the Neg. Ctrl group (dark triangles) after methacholine challenge. Mice treated with OVA+a4-vFLIP (open triangle) showed a statistically significant reduction in AHR (P<0.003) compared to OVA+TAT pep (open diamond), a group treated with an irrelevant peptide. Therefore, the autophagy peptide inducer a4-vFLIP was able to reduce AHR after OVA challenge.
Figures 9A, 9B, 9C:
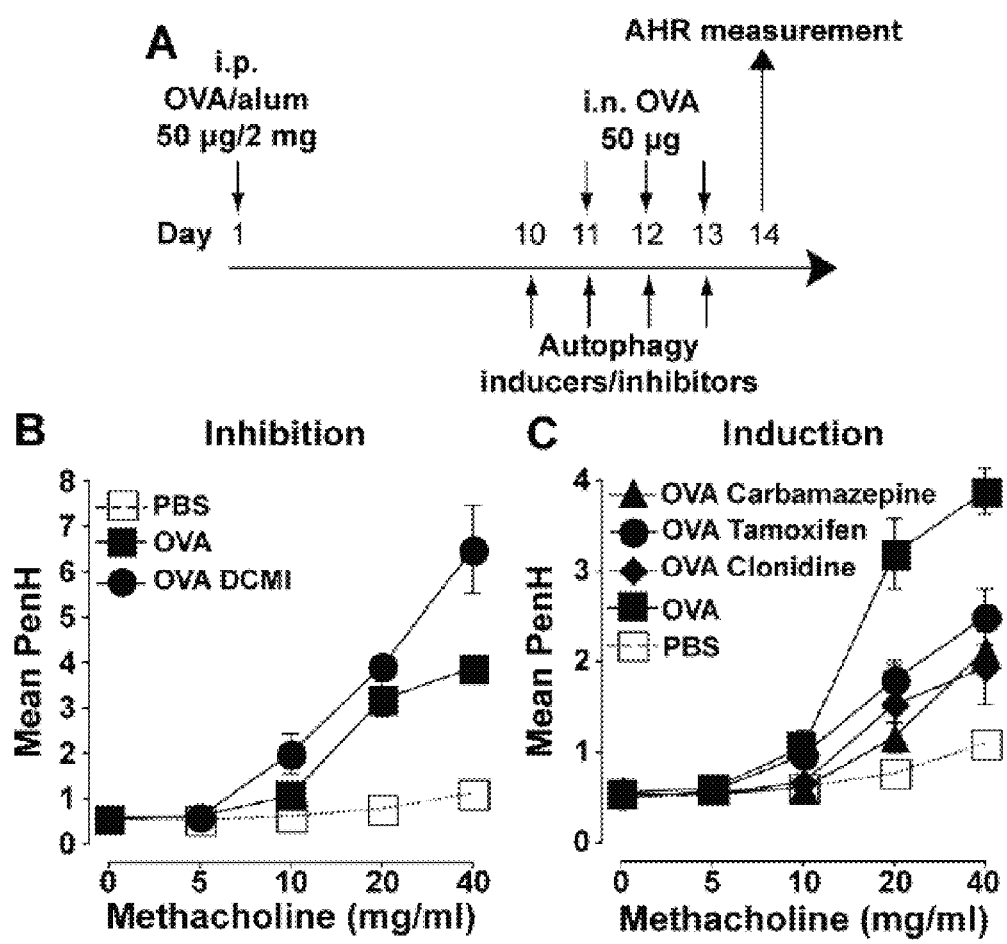
FIGS. 9A to 9C shows pharmacological modulation of AHR. Autophagy inducers (Carbamazepin, Tamoxifen, and Clonidine) and inhibitors (DCMI) were administered on days 10 to 13 (FIG. 9A). After increasing doses of Methacholine, the OVA DCMI treated group showed a significant increase in PenH compared to the OVA treated group (FIG. 9B). This was the opposite when treated with the autophagy inducers (Carbamazepin, Tamoxifen, and Clonidine) (FIG. 9C). Therefore, autophagy is an important mediator in AHR.
Figure 9D:
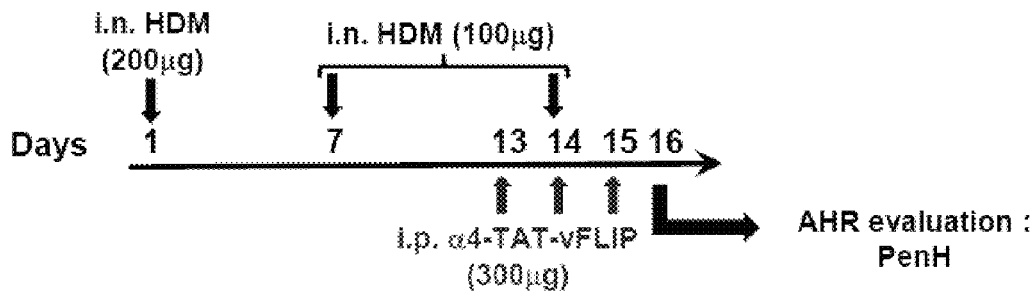
FIG. 9D illustrates a protocol to induce acute AHR by HDM. On day 1, naïve BALB/c mice (N=5 per group) received an intranasal (i.n.) injection with house dust mite (HDM) (200 m). After resting for 6 days, mice were treated intranasally (i.n.) with HDM (100 m) from days 7 to 14 and i.p. with the autophagy inducer a4-TAT-vFLIP (300 μg) on days 13 to 15. On day 16, the enhanced pause (PenH) variable was measured to determine airway hyperreactivity (AHR).
Figure 9E:
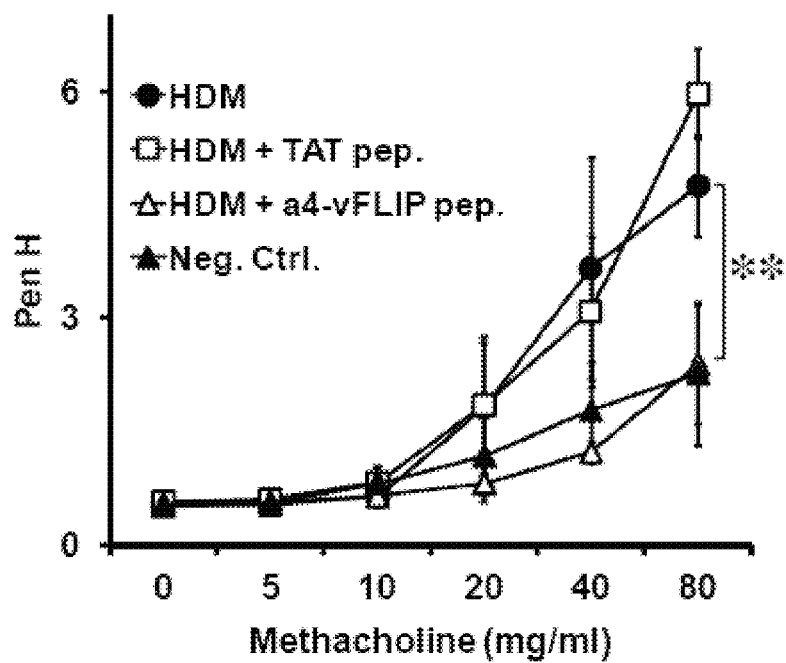
FIG. 9E shows that administration of vFLIP restore lung function in an acute model HDM induced asthma. Increasing doses of methacholine, a muscarinic receptor agonist to induce AHR, was administered to the different treatment groups of mice and the PenH was determined. HDM (dark circles) treated mice exhibited increased AHR compared to the Neg. Ctrl group (dark triangles) after methacholine challenge. Mice treated with HDM+a4-vFLIP (open triangle) showed a statistically significant reduction in AHR (P<0.003) compared to HDM+TAT pep (open square), a group treated with an irrelevant peptide. Therefore, the autophagy peptide inducer was able to reduce AHR after HDM challenge.

This experiment will identify the candidate pharmacological agents which can correct the defect in autophagy regulation in samples from asthma patients, see, for FIG. 7A showing an experimental protocol for testing FLIP peptides (disclosed in WO 2010/011952 A2 and PCT International Appl. No. PCT/US2011/045406, filed Jul. 27, 2010) as potent asthma pharmacological agents. FIG. 7B shows use of a FLIP peptide to treat asthma.

FLIP peptides are shown in Tables 1 to 5, below.

TABLE 1

| SEQ ID NO. | AMINO ACID SEQUENCE (Native Source) |
|---|---|
| 1 | EVVLFLLNVF (α2 region of KSHV vFLIP: amino acids 20-29) |
| 2 | QTFLHWVYCMEN (α4 region of KSHV vFLIP: amino acids 128-139) |
| 3 | EMLLFLCRDV (α2 region of cFLIP Short: amino acids 19-28) |
| 4 | KSFLDLVVELEK (α4 region of cFLIP Short: amino acids 128-139) |
| 5 | YCLLFLINGC (α2 region of HVS vFLIP: amino acids 20-29) |
| 6 | SSVILCVFSNML (α4 region of HVS vFLIP: amino acids 128-139) |
| 7 | SLLLFLCHDA (α2 region of MCV vFLIP: amino acids 26-35) |
| 8 | SRFVELVLALEN (α4 region of MCV vFLIP: amino acids 134-145) |

TABLE 2

| SEQ ID NO. | AMINO ACID SEQUENCE (Native Source) |
|---|---|
| 9 | MSAEVIHQVEEALDTDEKEMLLFLCRDVAIDVVPPNVRDLLD ILRERGKLSVGDLAELLYRVRRFDLLKRILKMDRKAVETHLL RNPHLVSDYRVLMAEIGEDLDKSDVSSLIFLMKDYMGRGKIS KEKSFLDLVVELEKLNLVAPDQLDLLEKCLKNIHRIDLKTKIQ KYKQSVQGAGTSYRNVLQAAIQKSLKDPSNNFRLHNGRSKE QRLKEQLGAQQEPVKKSIQESEAFLPQSIPEERYKMKSKPLGI CLIIDCIGNETELLRDTFTSLGYEVQKFLHLSMHGISQILGQFA CMPEHRDYDSFVCVLVSRGGSQSVYGVDQTHSGLPLHHIRR MFMGDSCPYLAGKPKMFFIQNYVVSEGQLEDSSLLEVDGPA MKNVEFKAQKRGLCTVHREADFFWSLCTADMSLLEQSHSSP SLYLQCLSQKLRQERKRPLLDLHIELNGYMYDWNSRVSAKE KYYVWLQHTLRKKLILSYT (cFLIP Long "cFLIP$_L$") |
| 10 | MATYEVLCEVARKLGTDDREVVLFLLNVFIPQPTLAQLIGAL RALKEEGRLTFPLLAECLFRAGRRDLLRDLLHLDPRFLERHLA GTMSYFSPYQLTVLHVDGELCARDIRSLIFLSKDTIGSRSTPQT FLHWVYCMENLDLLGPTDVDALMSMLRSLSRVDLQRQVQTL MGLHLSGPSHSQHYRHTP (KSHV vFLIP) |
| 11 | MDLKTTVLHITDSFTEEEMYCLLFLINGCIPRNCNAVKISDLIIE TLSKSTQWDICLTQCLYVLRKIELLLNLFQVTKEDVKQSFFTQ LQLETHVLTLVNVNNNLTAKDEKRLCFILDQFFPRNVVASSVI LCVFSNMLCEMPVLECLCQLKKCLKQIGRSDLAKTV (HVS vFLIP) |
| 12 | MSDSKEVPSLPFLRHLLEELDSHEDSLLLFLCHDAAPGCTTVT QALCSLSQQRKLTLAALVEMLYVLQRMDLLKSRFGLSKEGA EQLLGTSFLTRYRKLMVCVGEELDSSELRALRLFACNLNPSLS TALSESSRFVELVLALENVGLVSPSSVSVLADMLRTLRRLDLC QQLVEYEQQEQARYRYCYAASPSLPVRTLRRGHGASEHEQL CMPVQESSDSPELLRTPVQESSSDSPEQTT (MCV vFLIP) |

TABLE 2-continued

| SEQ ID NO. | AMINO ACID SEQUENCE (Native Source) |
|---|---|
| 13 | MSAEVIHQVEEALDTDEKEMLLFLCRDVAIDVVPPNVRDLLD ILRERGKLSVGDLAELLYRVRRFDLLKRILKMDRKAVETHLL RNPHLVSDYRVLMAEIGEDLDKSDVSSLIFLMKDYMGRGKIS KEKSFLDLVVELEKLNLVAPDQLDLLEKCLKNIHRIDLKTKIQ KYKQSVQGAGTSYRNVLQAAIQKSLKDPSNNFRMITPYAHCP DLKILGNCSM (cFLIP Short "cFLIPs") |

TABLE 3

| SEQ ID NO. | D- ISOMER RETRO-INVERSO PEPTIDES (Native Source) |
|---|---|
| 14 | RRRQRRKKRGY-G (TAT -DOMAIN) |
| 15 | RRRQRRKKRGY-G-FVNLLFLVVE (TAT -α2) |
| 16 | RRRQRRKKRGY-G-FVNLAAAVVE (TAT -α2m) |
| 17 | RRRQRRKKRGY-G- NEMCYVWHLFTQ (TAT -α2) |
| 18 | RRRQRRKKRGY-G- NEMCAAAHAATQ (TAT -α4M) |
| 28 | RRRQRRKKRGY-G-LMNSFVCLIVSS (24aa) (a4-vFLIP) |

TABLE 4

| SEQ ID NO. | AMINO ACID SEQUENCE (Native Source) |
|---|---|
| 19 | ILQTRTYDLYITYDKYYQTPRLWLFGYDEQRQPLTVEHMYED ISQDHVKKTVTIENHPHLPPPPMCSVHPCRHAEV (Atg3 Binding Domain) |
| 20 | VMKKIIETVAEGGGELGVHMYLLIFLKFVQAVIPTIEYDYTRH FTM (Atg3 Binding Domain) |

TABLE 5

| Name | SEQ ID NO | Sequence |
|---|---|---|
| M1 | 21 | SSVILCVYCMEN |
| M2 | 22 | QTFLHWVFSNML |
| M3 | 23 | QTFLLWVYCMEN |
| M4 | 24 | QTFLHCVYCMEN |
| M5 | 25 | QTFLLCVYCMEN |
| M6 | 26 | QTFLHWVYCMMN |
| M7 | 27 | QTFLLCVYCMMN |

Applicant will demonstrate that treatment of epithelial cells from asthma patients with autophagy inducers can correct the decrease in autophagic flux observed in lung biopsy samples from patients with asthma. From Applicant's preliminary studies in animal models, it has been demonstrated that treatment with autophagy inducers results in reduced AHR. Of particular interest for translation into clinical studies is that one of the inducers of autophagy that Applicant has used, carbamazepine, has previously been demonstrated to have high efficacy for the treatment of moderate to severe patients with asthma in a randomized placebo controlled double blind clinical trial (Lomia et al. (2006) Respir Med 100:1988-1996). This is of particular interest as carbamazepine and many of the other inducers Applicant has tested are already FDA approved for the treatment of other human conditions, allowing a more rapid progression into clinical trials for efficacy in asthma patients.

Epithelial cells from BAL and lung biopsy samples of asthma patients and normal individuals will be isolated by flow cytometric sorting (defined by size (FSC/SSC) and as CD45−). The purified epithelial cells will be cultured in the presence of autophagy inducers for up to 48 hours, which have demonstrated efficacy in our murine studies, such as carbamazepine and clonidine. Some of the cells will be harvested for autophagic flux determination by immunoblotting as described above. Another fraction will be used as antigen presenting cells in co-culture experiments with autologous CD4+ T cells, which will be isolated from paired peripheral blood samples using CD4 microbeads. Here, Applicant aims to test if by correction of the autophagy defect in the epithelial cells from asthma patients, reversal of the TH2 polarization can be acheived. T cells will be activated with either soluble anti-CD3 antibody (OKT3 clone at 2 µg/ml) or PHA-P (1 µg/ml) and cytokine secretion tested by intracellular staining and ELISA, focusing on IL-4, IL-13 and IFN-γ. It has previously been demonstrated that a functional autophagy pathway is required for mucus secretion by the paneth cells of the intestine (Hidvegi et al. (2010) Science 329:229-232), although no studies regarding the lungs have been reported. Applicant will therefore test mucus secretion by measuring MUC5AC in the supernatants from the epithelial cells of asthma patients and controls in the presence or absence of autophagy inducers (to correct asthma patient cells) or inhibitors (cause a defect in control cells).

Applicant expects to demonstrate that in vitro treatment of human cells with autophagy inducers such as carbamazepine and clonidine will correct the defect in autophagy as determined by autophagic flux measurements by immunoblotting. These results will serve as proof of principal for autophagy as a new therapeutic target for the treatment of asthma. Because Applicant will use freshly isolated primary human cells there are more technical challenges for the culture and treatment with these autophagy modifiers. Problems such as viability and contamination with bacteria and/or fungus may occur due to the nature of the site the cells are harvested from. However Applicant believes by performing the cultures for a short time (up to 48 hours) and in the presence of antibiotics and fungal treatments (gentamicin, ciprofloxacin and amphotericin B) Applicant can minimize these potential problems. It is possible that compounds such as carbamazepine or clonidine may not have that great of an effect on autophagy in human cells, or may not be able to achieve a high enough dose without causing a decrease in viability. As new compounds to modulate autophagy are constantly being developed new more specific pharmacological agents may arise. Applicant will perform characterization of these new compounds in the mouse but this time he will use the LC3eGFP knockin mouse (Mizushima et al. (2004) Mol Biol Cell 15:1101-1111) to allow the imaging of autophagic flux in real time in living cells.

Although the foregoing invention has been described in some detail by way of illustration and example for purposes of clarity of understanding, it will be apparent to those skilled in the art that certain changes and modifications will be practiced. Therefore, the description and examples should not be construed as limiting the scope of the invention, which is delineated by the appended claims.

What is claimed is:

1. A method for screening a compound or agent to treat asthma or a related disorder selected from the group of airway hyperreactivity (AHR), lung inflammation or respiratory tolerance, comprising administering to a transgenic mouse defective in autophagy protein 5 (Atg5), wherein the transgenic mouse expresses systemic or locally mutated Atg5 with reduced or abolished Atg5 expression, a candidate agent for an amount of time, and assaying for improved lung function by a method selected from the group of decreased airway resistance, decreased lung inflammation, increased autophagy in lung tissue, decreased cellular infiltration, decreased airway thickening, plethysmography, invasive plethysmography or T cell function in the mouse, wherein if the mouse has improved lung function, the compound or agent is a candidate for the treatment of asthma or a related disorder.

2. The method of claim 1, wherein the asthma is allergic asthma.

3. The method of claim 1, further comprising comparing the compound or agent that is a candidate for the treatment of asthma or a related disorder to an autophagy inducing agent selected from the group of carbomezepine, tamoxifen, minoxidil, erapumil, clonidine, and an autophagy inducing FLICE-like inhibitor protein (FLIP) peptide selected from the group of peptides identified by SEQ ID NO.: 1-8 or 14-28, or a peptide having at least 90% sequence identity to SEQ ID NO.: 1-8 or 14-28 and having the ability to induce autophagy.

4. The method of claim 3, wherein the peptide has at least 95% sequence identity to the FLIP peptide and has the ability to induce autophagy.

5. The method of claim 3, wherein the peptide having at least 90% sequence identity is a peptide coded by a polynucleotide that hybridizes to the coding or non-coding strand of a polynucleotide that encodes peptides identified by SEQ ID NO.: 1-8 or 14-28 under conditions of moderate or high stringency, wherein moderate stringency hybridization is typically performed at about 50° C. in about 6×SSC.

6. The method of claim 5, wherein the conditions of high stringency are at about 60° C. in about 1×SSC.

7. The method of any one of claim 1, 2, or 3, wherein the transgenic mouse defective in autophagy protein 5 (Atg5) function has a mutated or abolished Atg5 expression of greater than 90% in the lung and/or spleen.

* * * * *

SEQUENCE LISTING

```
<160> NUMBER OF SEQ ID NOS: 28

<210> SEQ ID NO 1
<211> LENGTH: 10
<212> TYPE: PRT
<213> ORGANISM: Human herpesvirus

<400> SEQUENCE: 1

Glu Val Val Leu Phe Leu Leu Asn Val Phe
1               5                   10

<210> SEQ ID NO 2
<211> LENGTH: 12
<212> TYPE: PRT
<213> ORGANISM: Human herpesvirus

<400> SEQUENCE: 2

Gln Thr Phe Leu His Trp Val Tyr Cys Met Glu Asn
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Met Leu Leu Phe Leu Cys Arg Asp Val
```

```
<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Ser Phe Leu Asp Leu Val Val Glu Leu Glu Lys
1               5                   10

<210> SEQ ID NO 5
<211> LENGTH: 10
<212> TYPE: PRT
<213> ORGANISM: Herpesvirus saimiri

<400> SEQUENCE: 5

Tyr Cys Leu Leu Phe Leu Ile Asn Gly Cys
1               5                   10

<210> SEQ ID NO 6
<211> LENGTH: 12
<212> TYPE: PRT
<213> ORGANISM: Herpesvirus saimiri

<400> SEQUENCE: 6

Ser Ser Val Ile Leu Cys Val Phe Ser Asn Met Leu
1               5                   10

<210> SEQ ID NO 7
<211> LENGTH: 10
<212> TYPE: PRT
<213> ORGANISM: Molluscum contagiosum virus

<400> SEQUENCE: 7

Ser Leu Leu Leu Phe Leu Cys His Asp Ala
1               5                   10

<210> SEQ ID NO 8
<211> LENGTH: 12
<212> TYPE: PRT
<213> ORGANISM: Molluscum contagiosum virus

<400> SEQUENCE: 8

Ser Arg Phe Val Glu Leu Val Leu Ala Leu Glu Asn
1               5                   10

<210> SEQ ID NO 9
<211> LENGTH: 480
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Ser Ala Glu Val Ile His Gln Val Glu Ala Leu Asp Thr Asp
1               5                   10                  15

Glu Lys Glu Met Leu Leu Phe Leu Cys Arg Asp Val Ala Ile Asp Val
                20                  25                  30

Val Pro Pro Asn Val Arg Asp Leu Leu Asp Ile Leu Arg Glu Arg Gly
            35                  40                  45
```

```
Lys Leu Ser Val Gly Asp Leu Ala Glu Leu Leu Tyr Arg Val Arg Arg
    50                  55                  60

Phe Asp Leu Leu Lys Arg Ile Leu Lys Met Asp Arg Lys Ala Val Glu
65                  70                  75                  80

Thr His Leu Leu Arg Asn Pro His Leu Val Ser Asp Tyr Arg Val Leu
                    85                  90                  95

Met Ala Glu Ile Gly Glu Asp Leu Asp Lys Ser Asp Val Ser Ser Leu
                100                 105                 110

Ile Phe Leu Met Lys Asp Tyr Met Gly Arg Gly Lys Ile Ser Lys Glu
                115                 120                 125

Lys Ser Phe Leu Asp Leu Val Val Glu Leu Glu Lys Leu Asn Leu Val
    130                 135                 140

Ala Pro Asp Gln Leu Asp Leu Leu Glu Lys Cys Leu Lys Asn Ile His
145                 150                 155                 160

Arg Ile Asp Leu Lys Thr Lys Ile Gln Lys Tyr Lys Gln Ser Val Gln
                165                 170                 175

Gly Ala Gly Thr Ser Tyr Arg Asn Val Leu Gln Ala Ala Ile Gln Lys
                180                 185                 190

Ser Leu Lys Asp Pro Ser Asn Asn Phe Arg Leu His Asn Gly Arg Ser
    195                 200                 205

Lys Glu Gln Arg Leu Lys Glu Gln Leu Gly Ala Gln Gln Glu Pro Val
    210                 215                 220

Lys Lys Ser Ile Gln Glu Ser Glu Ala Phe Leu Pro Gln Ser Ile Pro
225                 230                 235                 240

Glu Glu Arg Tyr Lys Met Lys Ser Lys Pro Leu Gly Ile Cys Leu Ile
                245                 250                 255

Ile Asp Cys Ile Gly Asn Glu Thr Glu Leu Leu Arg Asp Thr Phe Thr
                260                 265                 270

Ser Leu Gly Tyr Glu Val Gln Lys Phe Leu His Leu Ser Met His Gly
    275                 280                 285

Ile Ser Gln Ile Leu Gly Gln Phe Ala Cys Met Pro Glu His Arg Asp
    290                 295                 300

Tyr Asp Ser Phe Val Cys Val Leu Val Ser Arg Gly Gly Ser Gln Ser
305                 310                 315                 320

Val Tyr Gly Val Asp Gln Thr His Ser Gly Leu Pro Leu His His Ile
                325                 330                 335

Arg Arg Met Phe Met Gly Asp Ser Cys Pro Tyr Leu Ala Gly Lys Pro
                340                 345                 350

Lys Met Phe Phe Ile Gln Asn Tyr Val Val Ser Glu Gly Gln Leu Glu
    355                 360                 365

Asp Ser Ser Leu Leu Glu Val Asp Gly Pro Ala Met Lys Asn Val Glu
    370                 375                 380

Phe Lys Ala Gln Lys Arg Gly Leu Cys Thr Val His Arg Glu Ala Asp
385                 390                 395                 400

Phe Phe Trp Ser Leu Cys Thr Ala Asp Met Ser Leu Leu Glu Gln Ser
                405                 410                 415

His Ser Ser Pro Ser Leu Tyr Leu Gln Cys Leu Ser Gln Lys Leu Arg
                420                 425                 430

Gln Glu Arg Lys Arg Pro Leu Leu Asp Leu His Ile Glu Leu Asn Gly
    435                 440                 445

Tyr Met Tyr Asp Trp Asn Ser Arg Val Ser Ala Lys Glu Lys Tyr Tyr
    450                 455                 460
```

```
Val Trp Leu Gln His Thr Leu Arg Lys Lys Leu Ile Leu Ser Tyr Thr
465                 470                 475                 480
```

<210> SEQ ID NO 10
<211> LENGTH: 188
<212> TYPE: PRT
<213> ORGANISM: Human herpesvirus

<400> SEQUENCE: 10

```
Met Ala Thr Tyr Glu Val Leu Cys Glu Val Ala Arg Lys Leu Gly Thr
1               5                   10                  15

Asp Asp Arg Glu Val Val Leu Phe Leu Leu Asn Val Phe Ile Pro Gln
                20                  25                  30

Pro Thr Leu Ala Gln Leu Ile Gly Ala Leu Arg Ala Leu Lys Glu Glu
            35                  40                  45

Gly Arg Leu Thr Phe Pro Leu Leu Ala Glu Cys Leu Phe Arg Ala Gly
        50                  55                  60

Arg Arg Asp Leu Leu Arg Asp Leu Leu His Leu Asp Pro Arg Phe Leu
65                  70                  75                  80

Glu Arg His Leu Ala Gly Thr Met Ser Tyr Phe Ser Pro Tyr Gln Leu
                85                  90                  95

Thr Val Leu His Val Asp Gly Glu Leu Cys Ala Arg Asp Ile Arg Ser
                100                 105                 110

Leu Ile Phe Leu Ser Lys Asp Thr Ile Gly Ser Arg Ser Thr Pro Gln
            115                 120                 125

Thr Phe Leu His Trp Val Tyr Cys Met Glu Asn Leu Asp Leu Leu Gly
        130                 135                 140

Pro Thr Asp Val Asp Ala Leu Met Ser Met Leu Arg Ser Leu Ser Arg
145                 150                 155                 160

Val Asp Leu Gln Arg Gln Val Gln Thr Leu Met Gly Leu His Leu Ser
                165                 170                 175

Gly Pro Ser His Ser Gln His Tyr Arg His Thr Pro
            180                 185
```

<210> SEQ ID NO 11
<211> LENGTH: 167
<212> TYPE: PRT
<213> ORGANISM: Herpesvirus saimiri

<400> SEQUENCE: 11

```
Met Asp Leu Lys Thr Thr Val Leu His Ile Thr Asp Ser Phe Thr Glu
1               5                   10                  15

Glu Glu Met Tyr Cys Leu Leu Phe Leu Ile Asn Gly Cys Ile Pro Arg
                20                  25                  30

Asn Cys Asn Ala Val Lys Ile Ser Asp Leu Ile Ile Glu Thr Leu Ser
            35                  40                  45

Lys Ser Thr Gln Trp Asp Ile Cys Leu Thr Gln Cys Leu Tyr Val Leu
        50                  55                  60

Arg Lys Ile Glu Leu Leu Leu Asn Leu Phe Gln Val Thr Lys Glu Asp
65                  70                  75                  80

Val Lys Gln Ser Phe Phe Thr Gln Leu Gln Leu Glu Thr His Val Leu
                85                  90                  95

Thr Leu Val Asn Val Asn Asn Asn Leu Thr Ala Lys Asp Glu Lys Arg
                100                 105                 110

Leu Cys Phe Ile Leu Asp Gln Phe Phe Pro Arg Asn Val Val Ala Ser
            115                 120                 125
```

```
Ser Val Ile Leu Cys Val Phe Ser Asn Met Leu Cys Glu Met Pro Val
    130                 135                 140

Leu Glu Cys Leu Cys Gln Leu Lys Lys Cys Leu Lys Gln Ile Gly Arg
145                 150                 155                 160

Ser Asp Leu Ala Lys Thr Val
                165

<210> SEQ ID NO 12
<211> LENGTH: 241
<212> TYPE: PRT
<213> ORGANISM: Molluscum contagiosum virus

<400> SEQUENCE: 12

Met Ser Asp Ser Lys Glu Val Pro Ser Leu Pro Phe Leu Arg His Leu
1               5                   10                  15

Leu Glu Glu Leu Asp Ser His Glu Asp Ser Leu Leu Phe Leu Cys
                20                  25                  30

His Asp Ala Ala Pro Gly Cys Thr Thr Val Thr Gln Ala Leu Cys Ser
                35                  40                  45

Leu Ser Gln Gln Arg Lys Leu Thr Leu Ala Ala Leu Val Glu Met Leu
    50                  55                  60

Tyr Val Leu Gln Arg Met Asp Leu Leu Lys Ser Arg Phe Gly Leu Ser
65                  70                  75                  80

Lys Glu Gly Ala Glu Gln Leu Leu Gly Thr Ser Phe Leu Thr Arg Tyr
                85                  90                  95

Arg Lys Leu Met Val Cys Val Gly Glu Glu Leu Asp Ser Ser Glu Leu
                100                 105                 110

Arg Ala Leu Arg Leu Phe Ala Cys Asn Leu Asn Pro Ser Leu Ser Thr
                115                 120                 125

Ala Leu Ser Glu Ser Ser Arg Phe Val Glu Leu Val Ala Leu Glu
    130                 135                 140

Asn Val Gly Leu Val Ser Pro Ser Ser Val Ser Val Leu Ala Asp Met
145                 150                 155                 160

Leu Arg Thr Leu Arg Arg Leu Asp Leu Cys Gln Gln Leu Val Glu Tyr
                165                 170                 175

Glu Gln Gln Glu Gln Ala Arg Tyr Arg Tyr Cys Tyr Ala Ala Ser Pro
                180                 185                 190

Ser Leu Pro Val Arg Thr Leu Arg Arg Gly His Gly Ala Ser Glu His
                195                 200                 205

Glu Gln Leu Cys Met Pro Val Gln Glu Ser Ser Asp Ser Pro Glu Leu
    210                 215                 220

Leu Arg Thr Pro Val Gln Glu Ser Ser Asp Ser Pro Glu Gln Thr
225                 230                 235                 240

Thr

<210> SEQ ID NO 13
<211> LENGTH: 221
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Ser Ala Glu Val Ile His Gln Val Glu Glu Ala Leu Asp Thr Asp
1               5                   10                  15

Glu Lys Glu Met Leu Leu Phe Leu Cys Arg Asp Val Ala Ile Asp Val
```

```
                    20                  25                  30
Val Pro Pro Asn Val Arg Asp Leu Leu Asp Ile Leu Arg Glu Arg Gly
                35                  40                  45

Lys Leu Ser Val Gly Asp Leu Ala Glu Leu Leu Tyr Arg Val Arg Arg
         50                  55                  60

Phe Asp Leu Leu Lys Arg Ile Leu Lys Met Asp Arg Lys Ala Val Glu
 65                  70                  75                  80

Thr His Leu Leu Arg Asn Pro His Leu Val Ser Asp Tyr Arg Val Leu
                 85                  90                  95

Met Ala Glu Ile Gly Glu Asp Leu Asp Lys Ser Asp Val Ser Ser Leu
            100                 105                 110

Ile Phe Leu Met Lys Asp Tyr Met Gly Arg Gly Lys Ile Ser Lys Glu
        115                 120                 125

Lys Ser Phe Leu Asp Leu Val Val Glu Leu Glu Lys Leu Asn Leu Val
    130                 135                 140

Ala Pro Asp Gln Leu Asp Leu Leu Glu Lys Cys Leu Lys Asn Ile His
145                 150                 155                 160

Arg Ile Asp Leu Lys Thr Lys Ile Gln Lys Tyr Lys Gln Ser Val Gln
                165                 170                 175

Gly Ala Gly Thr Ser Tyr Arg Asn Val Leu Gln Ala Ala Ile Gln Lys
            180                 185                 190

Ser Leu Lys Asp Pro Ser Asn Asn Phe Arg Met Ile Thr Pro Tyr Ala
        195                 200                 205

His Cys Pro Asp Leu Lys Ile Leu Gly Asn Cys Ser Met
    210                 215                 220

<210> SEQ ID NO 14
<211> LENGTH: 12
<212> TYPE: PRT
<213> ORGANISM: Human immunodeficiency virus

<400> SEQUENCE: 14

Arg Arg Arg Gln Arg Arg Lys Lys Arg Gly Tyr Gly
1               5                   10

<210> SEQ ID NO 15
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Arg Arg Gln Arg Arg Lys Lys Arg Gly Tyr Gly Phe Val Asn Leu
1               5                   10                  15

Leu Phe Leu Val Val Glu
            20

<210> SEQ ID NO 16
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Arg Arg Gln Arg Arg Lys Lys Arg Gly Tyr Gly Phe Val Asn Leu
1               5                   10                  15
```

```
Ala Ala Ala Val Val Glu
            20

<210> SEQ ID NO 17
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Arg Arg Gln Arg Arg Lys Lys Arg Gly Tyr Gly Asn Glu Met Cys
1               5                   10                  15

Tyr Val Trp His Leu Phe Thr Gln
            20

<210> SEQ ID NO 18
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Arg Arg Gln Arg Arg Lys Lys Arg Gly Tyr Gly Asn Glu Met Cys
1               5                   10                  15

Ala Ala His Ala Ala Thr Gln
            20

<210> SEQ ID NO 19
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ile Leu Gln Thr Arg Thr Tyr Asp Leu Tyr Ile Thr Tyr Asp Lys Tyr
1               5                   10                  15

Tyr Gln Thr Pro Arg Leu Trp Leu Phe Gly Tyr Asp Glu Gln Arg Gln
            20                  25                  30

Pro Leu Thr Val Glu His Met Tyr Glu Asp Ile Ser Gln Asp His Val
        35                  40                  45

Lys Lys Thr Val Thr Ile Glu Asn His Pro His Leu Pro Pro Pro Pro
    50                  55                  60

Met Cys Ser Val His Pro Cys Arg His Ala Glu Val
65                  70                  75

<210> SEQ ID NO 20
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Val Met Lys Lys Ile Ile Glu Thr Val Ala Glu Gly Gly Gly Glu Leu
1               5                   10                  15

Gly Val His Met Tyr Leu Leu Ile Phe Leu Lys Phe Val Gln Ala Val
```

```
                20                  25                  30
Ile Pro Thr Ile Glu Tyr Asp Tyr Thr Arg His Phe Thr Met
        35                  40                  45

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Ser Val Ile Leu Cys Val Tyr Cys Met Glu Asn
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Thr Phe Leu His Trp Val Phe Ser Asn Met Leu
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gln Thr Phe Leu Leu Trp Val Tyr Cys Met Glu Asn
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Thr Phe Leu His Cys Val Tyr Cys Met Glu Asn
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gln Thr Phe Leu Leu Cys Val Tyr Cys Met Glu Asn
1               5                   10

<210> SEQ ID NO 26
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 26

Gln Thr Phe Leu His Trp Val Tyr Cys Met Met Asn
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gln Thr Phe Leu Leu Cys Val Tyr Cys Met Met Asn
1               5                   10

<210> SEQ ID NO 28
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Arg Arg Gln Arg Arg Lys Lys Arg Gly Tyr Gly Leu Met Asn Ser
1               5                   10                  15

Phe Val Cys Leu Ile Val Ser Ser
            20
```